(12) United States Patent
Thorson

(10) Patent No.: US 7,259,141 B2
(45) Date of Patent: Aug. 21, 2007

(54) VANCOMYCIN ANALOGS AND METHODS THEREOF

(75) Inventor: Jon S. Thorson, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 69 days.

(21) Appl. No.: 10/908,624

(22) Filed: May 19, 2005

(65) Prior Publication Data

US 2005/0239689 A1 Oct. 27, 2005

Related U.S. Application Data

(63) Continuation-in-part of application No. 10/670,073, filed on Sep. 24, 2003, which is a continuation-in-part of application No. 10/109,672, filed on Apr. 1, 2002, now Pat. No. 6,884,604.

(60) Provisional application No. 60/279,682, filed on Mar. 30, 2001.

(51) Int. Cl.
A61K 38/16 (2006.01)
A61K 31/70 (2006.01)
A01N 43/04 (2006.01)
C07H 17/00 (2006.01)
C07G 11/00 (2006.01)

(52) U.S. Cl. ............... 514/8; 514/1; 514/23; 514/25; 536/4.1; 536/16.8

(58) Field of Classification Search ......... 514/2, 514/25, 1, 23; 536/4.1, 16.8
See application file for complete search history.

(56) References Cited

U.S. PATENT DOCUMENTS 6,498,238 B1 * 12/2002 Kim et al. ............... 536/16.8
6,699,836 B2 * 3/2004 Kahne et al. ............ 514/7
6,884,604 B2 4/2005 Thorson

OTHER PUBLICATIONS

Ahrendt, K.A., et al., A. Bioorg. Med. Chem. Lett., 13:1683 (2003).
Akerfeldt, S., J. Med Chem. 13:1012 (1970).
Albermann, C., et al., Org. Lett. 5:933 (2003).
Baltz, R.H., Chem. Biol., 9:1268 (2002).
Barton, W.A. et al., Proc. Natl. Acad. Sci USA 99:13397 (2002).
Barton, W. A., et al., Nat. Struct. Biol.8:545 (2001).
Boger, D. L. et al., J. Am Chem Soc. 120:8920 (1998).
Deng, H.B. et al., J. Am. Chem. Soc. 125:9032 (2003).
Dong, S. D. et al., J. Am. Chem. Soc., 124:9064 (2002).
Fu, X., et al., Nat. Biotechnol. 21:1467 (2003).
Ge, M., et al., Science, 284:507 (1999).
Hlasta, D. J. and Acherman, J. H. J. Org. Chem 59:6184 (1994).
Hoffmeister, D., et al., ChemBioChem 5:989 (2004).
Hoffmeister, D., et al., Proc. Natl. Acad. Sci. USA 100:13184 (2003).
Hubbard, B. K. et al., Angew Chem. Int. Ed. 42:730 (2003).
Jain, R. K. et al., J. Am. Chem. Soc. 125:8740 (2003).
Jiang, J. et al., Angew. Chem.. Int. Ed. 40:1502 (2001).
Jiang, J., et al., ChemBioChem 4:443 (2003).
Kaplan, J. et al., J. Med. Chem. 44:1837 (2001).
Koegel, H. et al., J. Biol. Chem.. 278:3323 (2003).
Loll, P. J., et al., J. Med. Chem 42:4714 (1999).
Losey, H. C. et al., Biochemistry 40:4745 (2001).
Mu, Y., et al., Mu, Y., et al., A. Biorg. Med. Chem. Lett., 14:735 (2004).
Seo, T.S. et al., J. Org Chem, 68:609 (2003).
Sharman, G. J. et al., J. Am Chem. Soc. 119:12041 (1997).
Shiozawa, H., et al., J. Am. Chem. Soc. 124:3914 (2002).
Singh, S.B. et al., J. Nat. Prod. 64:874 (2001).
Sun, B. , et al., J. Am. Chem. Soc. 123:12722 (2001).
Thorson, J. S. et al., ChemBioChem 5:16 (2004).
Walsh, C. T., et al., J. Med. Chem., 46:3425 (2003).
Wang, Q, et al., J. Am. Chem Soc. 125:3192 (2003).
Williams, D. H., et al., Science 280:711 (1998).
Yang, J. et al., Biorg. Med Chem. 12:1577 (2004).
Yang, J. et al., ChemBioChem 5:992 (2004).
Yang, J. et al., Org. Lett. 5:2223 (2003).
Losey, J.C. et al., Chem Biol. 12:1305 (2002).
Nicolaou, K.C., et al., Angew. Chem. Int. Ed. 38:2096 (1999).
Nagarajan, R. et al., Antibiot. 42:63 (1989).
Rostovtsev, V.V. et al, Angew. Chem.. Int. Ed. 41:2596 (2002).
Strahilevitz, J. and Rubinstein, E., Int J. Infect. Dis. Suppl 1 S38 (2003).

* cited by examiner

*Primary Examiner*—Shaojia Anna Jiang
*Assistant Examiner*—Traviss McIntosh
(74) *Attorney, Agent, or Firm*—Quarles & Brady LLP

(57) ABSTRACT

The present invention provides vancomycin analogs and methods related to synthesis of these analogs via chemoenzymatic techniques. In a preferred embodiment, the vancomycin analogs have a structural moiety selected from the group consisting of:

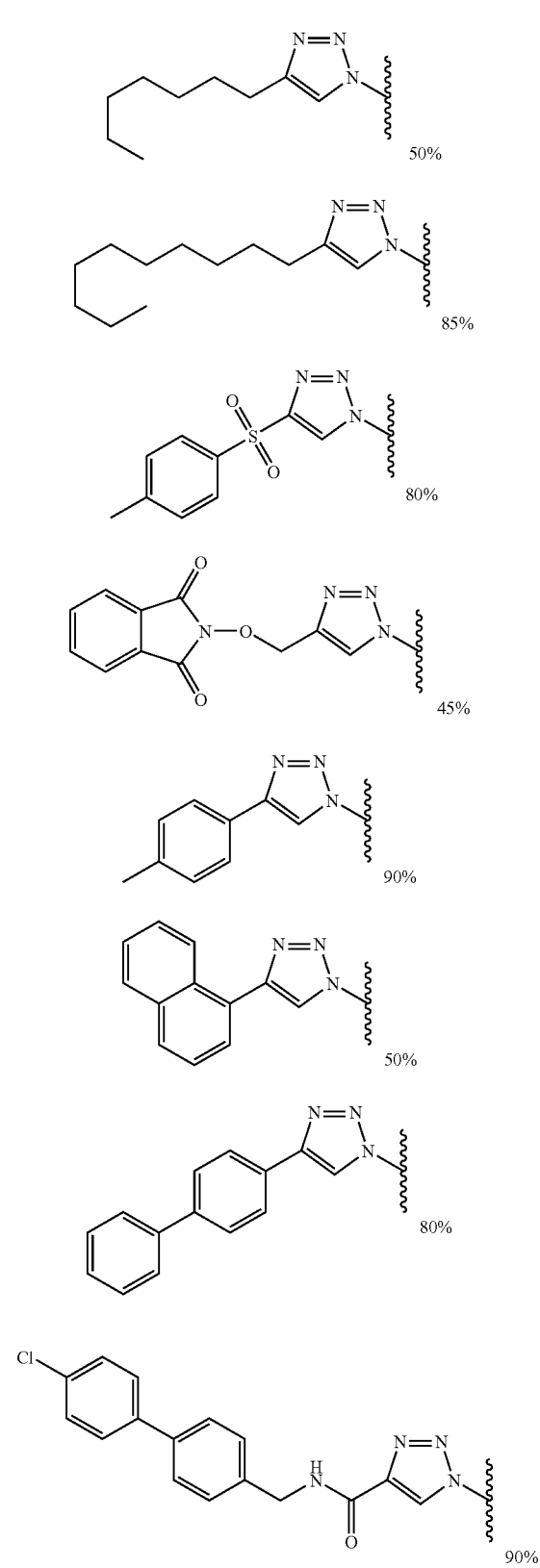
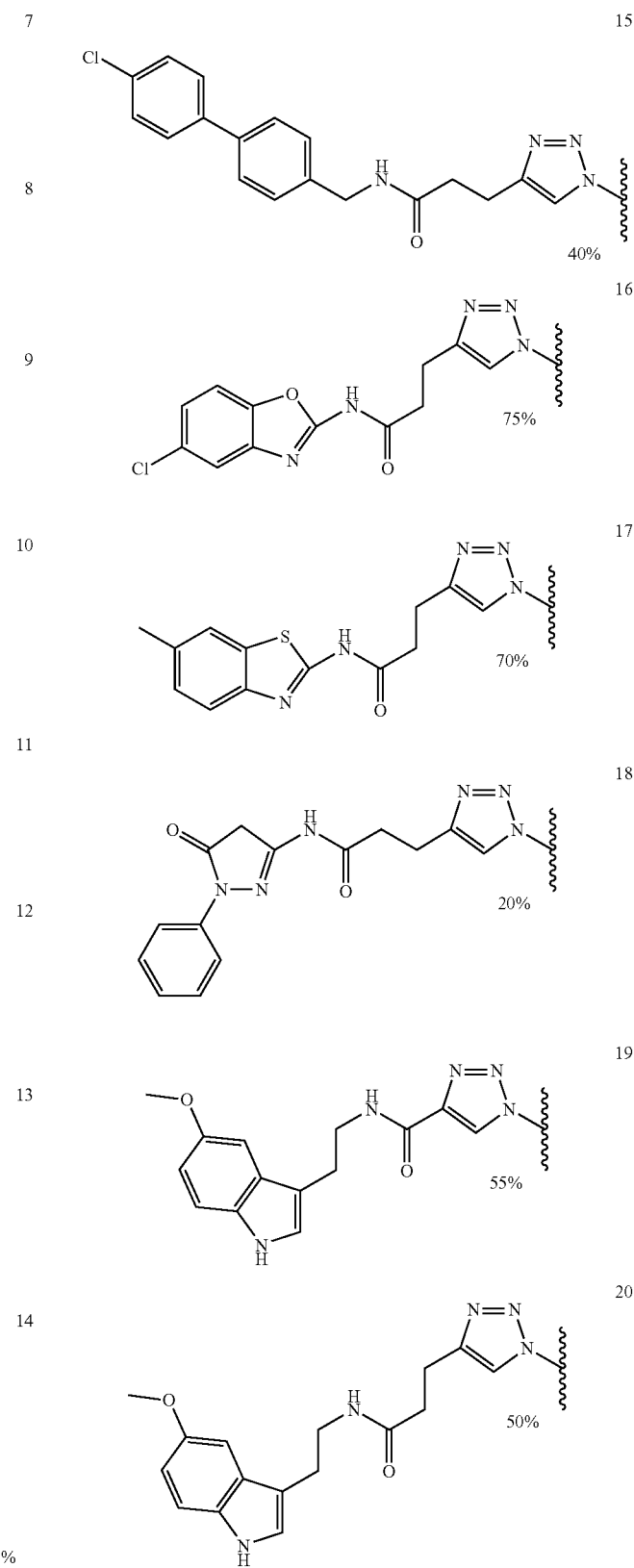

-continued
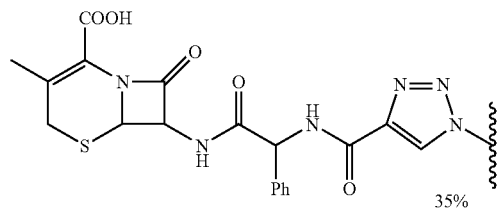
21
35%
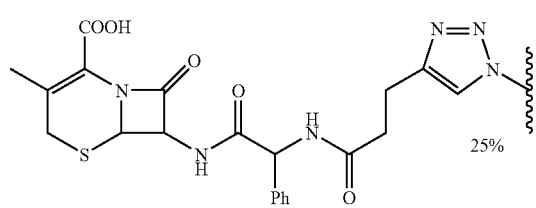
22
25%
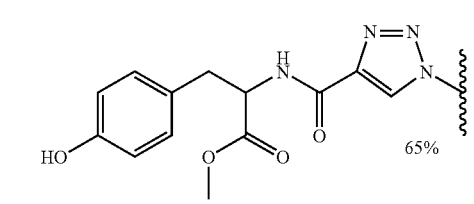
23
65%
-continued
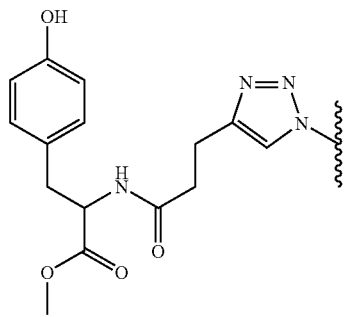
24
80% and
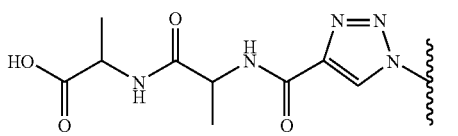
25
70%.
4 Claims, 6 Drawing Sheets

| Compound | *S. aureus* (ATCC 700699) | *E. faecalis* (ATCC 700802) | *E. faecium* (ATCC 700221) |
|---|---|---|---|
| Van | 12±3 | 23±4 | 23±2 |
| 3 | 21±3 | 21±2 | 23±5 |
| 6 | 11±4 | 10±1 | 10±3 |
| 7 | 7±1 | 12±1 | 11±2 |
| 8 | 13±3 | >24 | >24 |
| 21 | >24 | 16±1 | 12±2 |
| 26 | 10±1 | 20±3 | 19±2 |
| | Range = 6-12 µg. | Range = 12-24 µg. | Range = 6-24 µg. |

FIG. 4

Product Characterization.

| Compound Entry | Calculated mass | Determined mass | Retention time[#] (min) | Yield[*] (%) |
|---|---|---|---|---|
| 4 | 1443.34 | 1444.39 | 15.70 | 30 |
| 5 | 1427.38 | 1428.40 | 15.82 | 50 |
| 6 | 1511.47 | 1512.50 | 17.90 | 70 |
| 7 | 1453.47 | 1454.47 | 19.63 | 50 |
| 8 | 1495.51 | 1496.52 | 21.08 | 85 |
| 9 | 1509.37 | 1510.37 | 19.80 | 80 |
| 10 | 1530.38 | 1531.37 | 18.89 | 45 |
| 11 | 1445.40 | 1446.41 | 25.10 | 90 |
| 12 | 1481.40 | 1482.42 | 22.65 | 50 |
| 13 | 1507.42 | 1508.42 | 19.70 | 80 |
| 14 | 1598.40 | 1599.42 | 20.27 | 90 |
| 15 | 1626.43 | 1627.40 | 20.15 | 40 |
| 16 | 1577.38 | 1578.38 | 20.03 | 75 |
| 17 | 1573.41 | 1574.42 | 20.31 | 70 |
| 18 | 1584.44 | 1585.46 | 22.22 | 20 |
| 19 | 1571.45 | 1572.46 | 19.89 | 55 |
| 20 | 1599.48 | 1600.48 | 19.53 | 50 |
| 21 | 1728.43 | 1729.46 | 19.48 | 35 |
| 22 | 1756.46 | 1757.50 | 19.25 | 25 |
| 23 | 1576.43 | 1577.43 | 19.11 | 65 |
| 24 | 1604.46 | 1605.47 | 18.83 | 80 |
| 25 | 1541.42 | 1542.45 | 15.44 | 70 |

[#]Retention time was determined on Luna C18, 5μm, 250 × 4.6 mm (Phenomenex) with 0.1% trifluoroacetic acid in $H_2O$ (A) and acetonitrile (B) as mobile phase. * Yield was proximally calculated from the HPLC peak area comparing with that of the starting azidosugar agalycon 3.

FIG. 7

VANCOMYCIN ANALOGS AND METHODS THEREOF

RELATED APPLICATIONS

The present invention is a continuation-in-part of U.S. patent application Ser. No. 10/670,073 filed on Sep. 24, 2003, which is a continuation-in-part of U.S. patent application Ser. No. 10/109,672 filed on Apr. 1, 2002 now U.S. Pat. No. 6,884,604, which in turn seeks priority from a provisional application No. 60/279,682 filed on Mar. 30, 2001, all of which are incorporated herein by reference in its entirety for all purposes.

STATEMENT REGARDING FEDERAL FUNDING

This work was supported in part by the National Institutes of Health (GM58196, CA84374, and AI52218). The Federal Government may have certain rights in this invention.

TECHNICAL FIELD

The present invention generally relates to vancomycin analogs and related methods of synthesis of these analogs. Specifically the invention relates to vancomycin analogs that are directed to vancomycin resistant enterecocci and staphylococci.

BACKGROUND

Vancomycin is a small glycopeptide and is considered an antibiotic of "last resort" for fighting infections by *Staphylococcus aureus* and *Clostridium difficile*. However, at the beginning of 1987, hospitals began reporting vancomycin resistant strains of enterococci. Vancomycin acts by interfering with the biosynthesis of the bacterial cell wall. It binds to the peptide substrates [Ala-Glu-Lys-Ala-Ala] and prevents it from cross-linking carbohydrates in the cell wall. Resistant bacteria, however, overcome vancomycin's effect by synthesizing [Ala-Glu-Lys-Ala-lactate]. Vancomycin does not bind well to this moiety; and therefore the bacterial cell wall is synthesized.

The emergence of vancomycin-resistant Enterococci and Staphylococci (VRE/VRS) clinical isolates in conjunction with the demonstrated antiviral properties of certain glycopeptides, continues to promote the search for efficient routes of rapid glycopeptide diversification.

The rapid diversification of glycopeptides via glycorandomization reveals significantly diverse substitutions are tolerated and suggests there may be a synergistic benefit to the construction of mechanistically—related natural product core scaffold fusions. Glycorandomization is a chemoenzymatic process in which scaffold of a natural compound is altered through alteration of its sugar moieties. Since sugar groups help determine biological activity in large number of pharmaceutically interesting compounds, glycorandomization is an important process in developing new therapeutic compounds.

Toward this goal, recent research has revealed that alterations to the vancomycin's L-vancosaminyl-1,2-D-glucosyl disaccharide attachment, via chemical or chemoenzymatic impacts upon both the molecular target and organism specificity.

However, the need exists for yet newer molecules and architecture, especially using chemoenzymatic approaches to diversify complex natural products that may be capable of countering the effects of vancomycin-resistant Enterococci and Staphylococci.

SUMMARY OF THE INVENTION

The present invention teaches rapid diversification of vancomycin analogs through glycorandomization and chemoenzymatic strategies resulting in a diverse library of complex natural product architectures. In a preferred embodiment, the present invention teaches a vancomycin analog having a structure of Formula I,

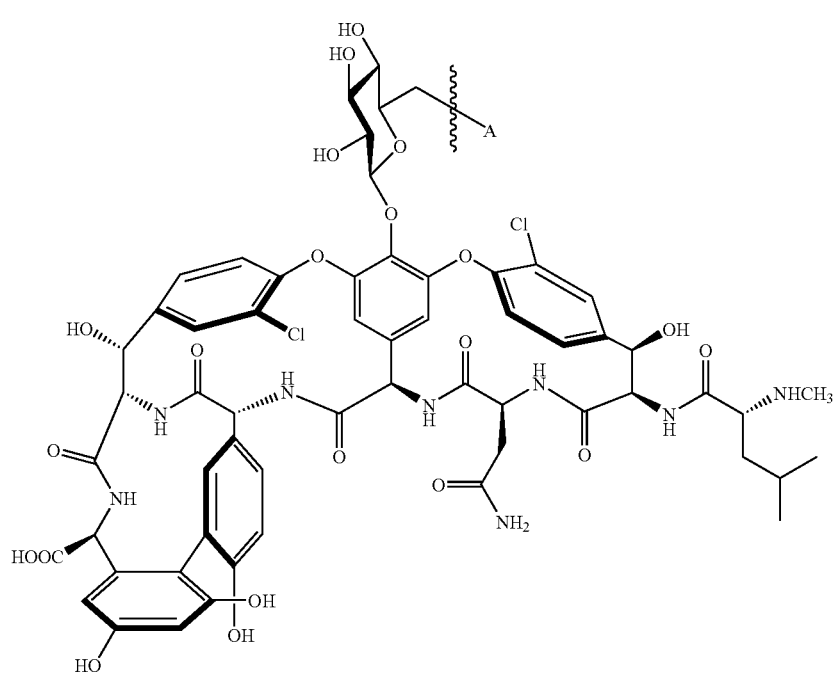

Formula I wherein the structural moiety "A" is selected from the group consisting of:
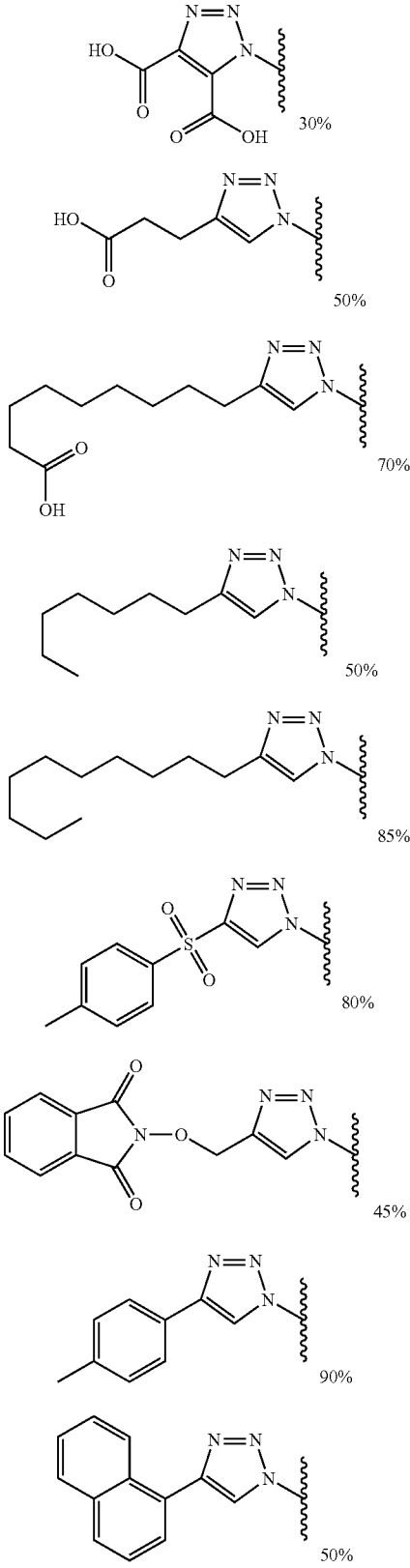
-continued
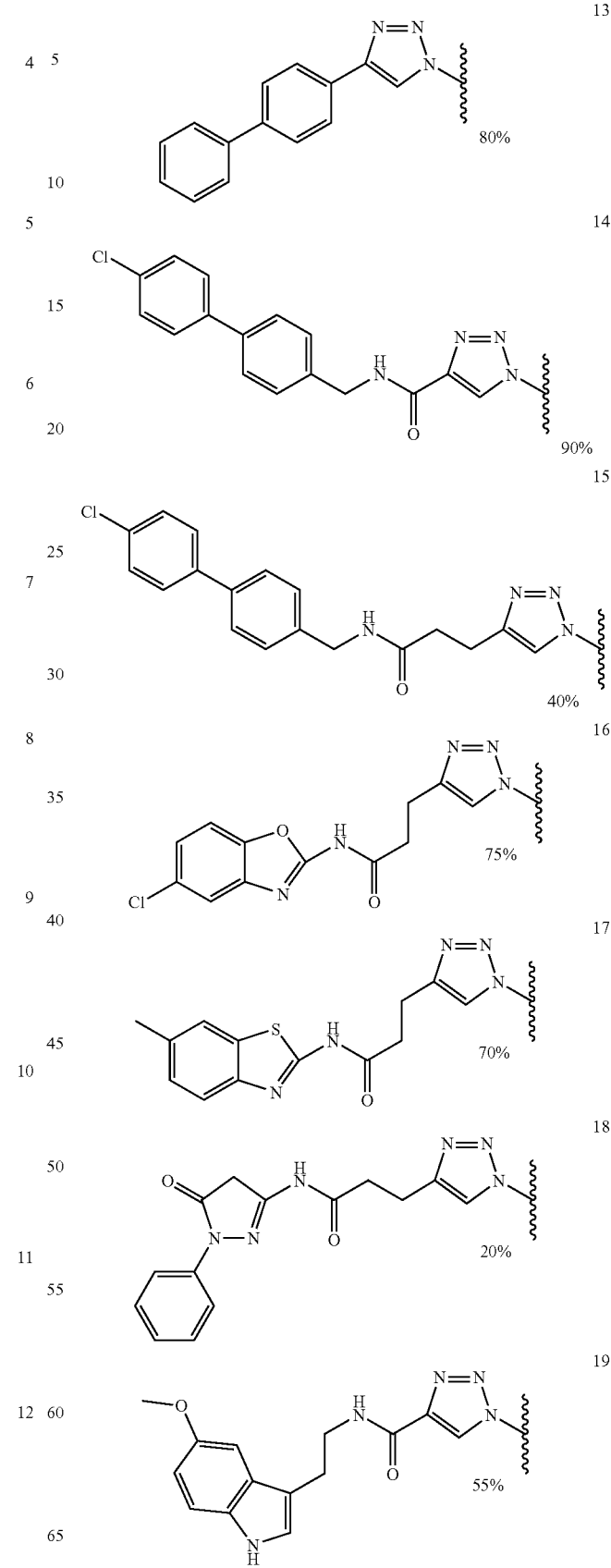

-continued

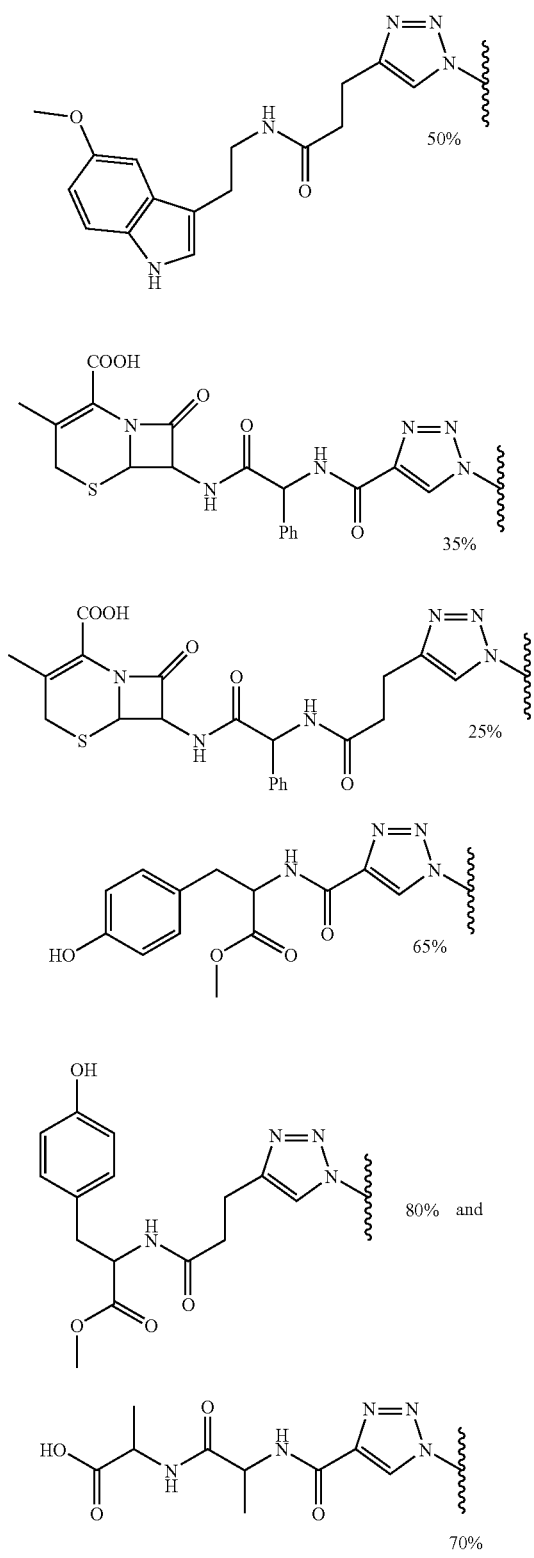

In this embodiment the analog is produced from a dipolar cycloaddition reaction with an alkyne. Preferably, the alkyne is $R_1$—C≡C—$R_2$, wherein $R_1$ is selected from a group consisting of:

and wherein $R_2$ is selected from a group consisting of:

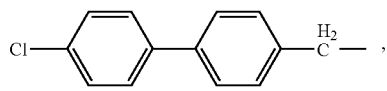

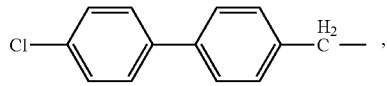

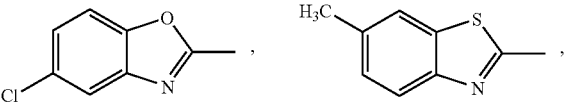

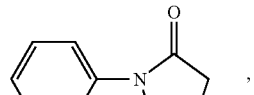

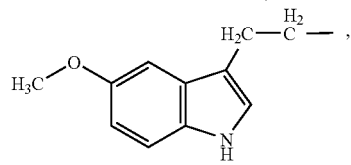

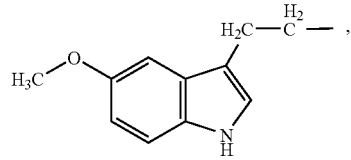

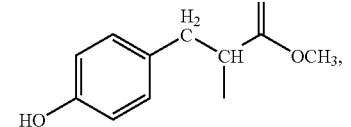

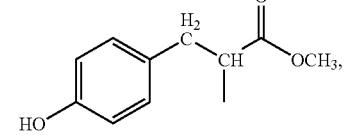

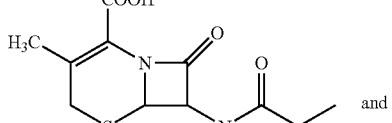

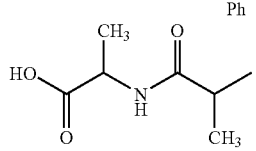

Yet another embodiment of the present invention provides a method for synthesizing a vancomycin analog. The method comprises the steps of:

(a) reacting a vancomycin aglycon with a sugar transferase; and
(b) further reacting the resulting compound from step (a) with an alkyne via a 1,3 dipolar cycloaddition to result in a vancomycin analog, such that the resulting vancomycin analog from step (b) has a structure of Formula I, as shown above and the structural moiety "A" is selected from the group consisting of:
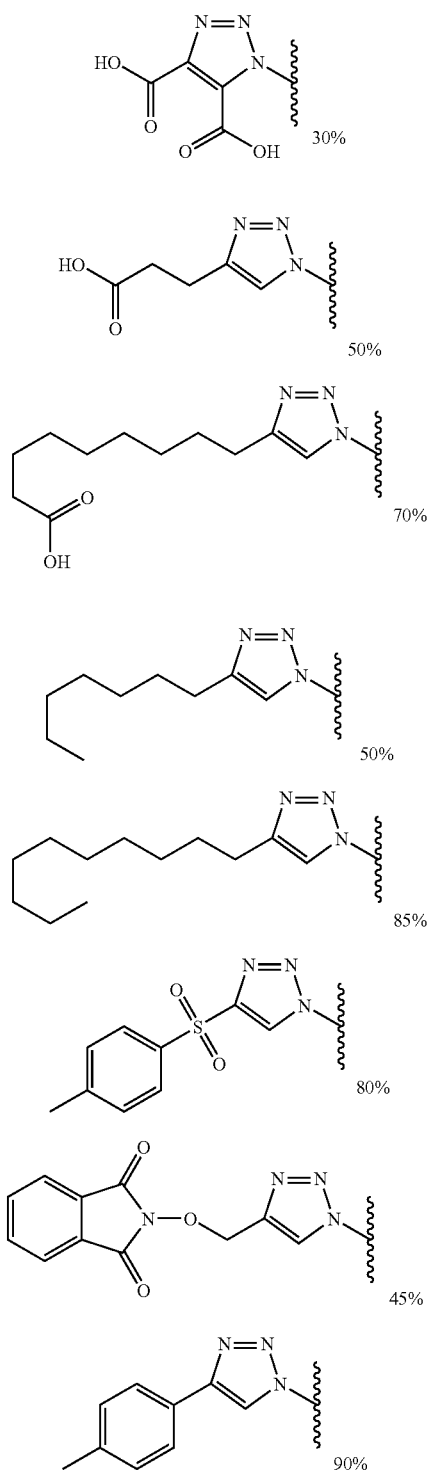
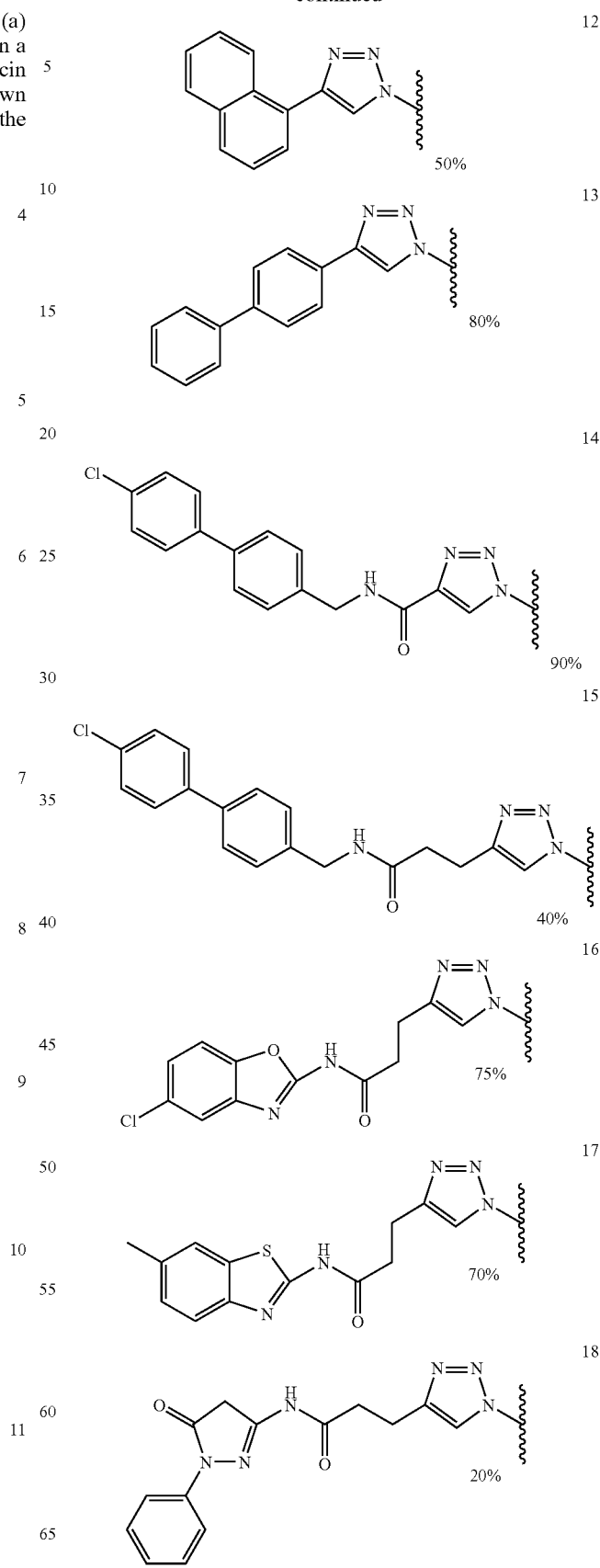

-continued
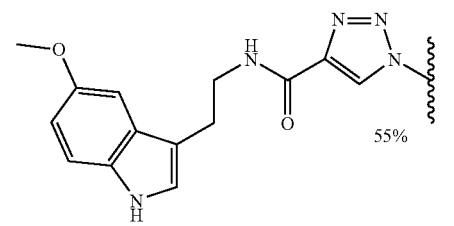
19
55%
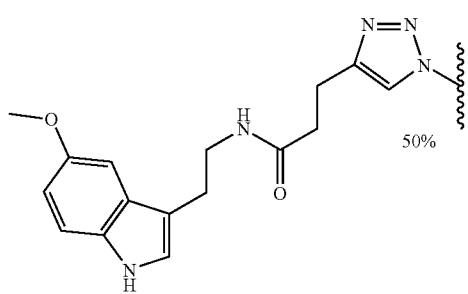
20
50%
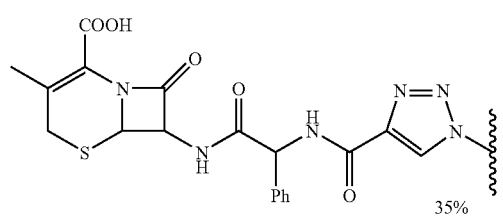
21
35%
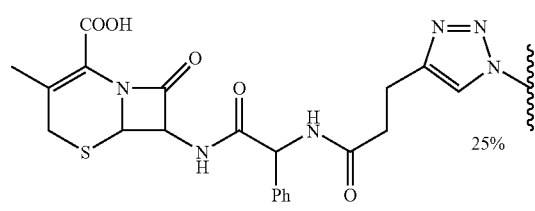
22
25%
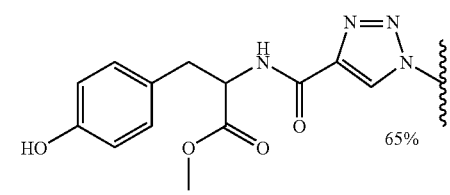
23
65%
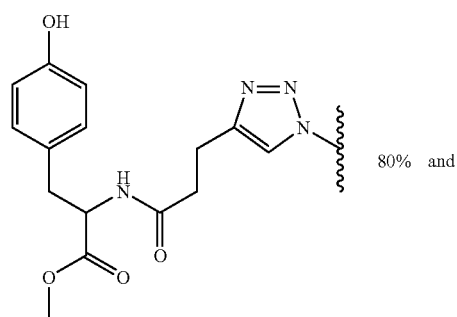
24
80% and
-continued
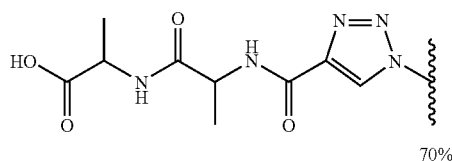
25
70%
In this embodiment as well, the alkyne is $R_1—C\equiv C—R_2$, wherein $R_1$ is selected from a group consisting of:
and wherein $R_2$ is selected from a group consisting of:
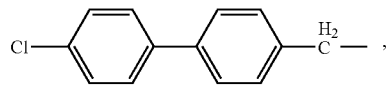
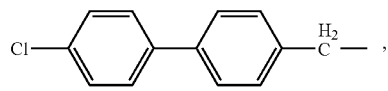
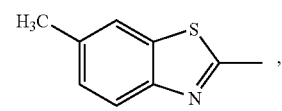
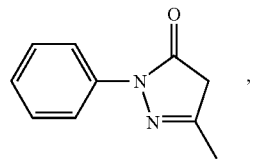
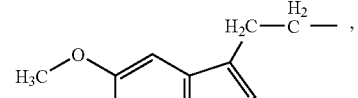
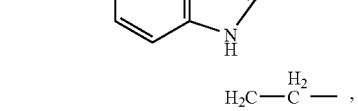
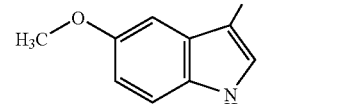
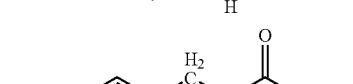
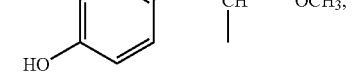
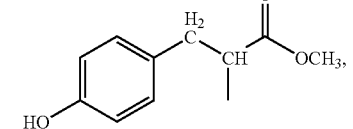

-continued

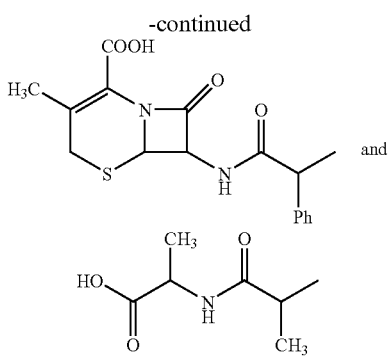

Preferably, in this method, the sugar transferase is GtfE.

Yet another embodiment of the present invention provides the use of the vancomycin analog of claim 1, salt or prodrug thereof for the production of a pharmaceutical composition for the treatment of vancomycin resistant Enterococci or vancomycin resistant Staphylococci.

Another embodiment of the present invention provides a method for prevention and/or treatment of vancomycin resistant Enterococci or vancomycin resistant Staphylococci in a subject. This method comprises the step of administering to the subject an effective amount of the vancomycin analog of claim 1, a pharmaceutically acceptable salt, or a prodrug thereof.

The present invention also provides a pharmaceutical composition comprising: (a) the vancomycin analog of claim 1; or (b) a pharmaceutically acceptable salt of said analog; or (c) a pharmaceutically acceptable prodrug of said analog; and (d) a pharmaceutically-acceptable carrier.

Other objects and advantages of the present invention will be apparent from the following detailed description, drawings and appended claims.

BRIEF DESCRIPTION OF THE DRAWINGS

FIG. 4 depicts a set of analogs that were tested for their antibacterial activity and those analogs showing favorable activities against methicillin-resistant S. aureus, vancomycin-sensitive E. faecalis and/or E. faecium.

FIG. 7 provides product characterization of certain analogs.

DETAILED DESCRIPTION OF THE PREFERRED EMBODIMENTS

A: General

Figure 1:
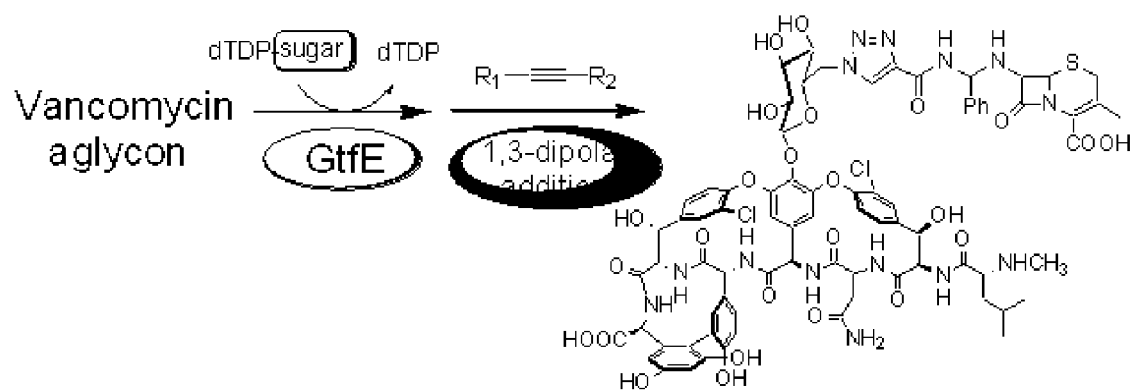
FIG. 1 depicts diversification of glycopeptides via glycorandomization.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

B. Preferred Embodiments

As defined herein, the term "compound" includes the above described structures and its pharmaceutically acceptable salts, metabolites, hydrates, isomers and derivatives.

As defined herein, the term "isomer" includes, but is not limited to optical isomers and analogs, structural isomers and analogs, conformational isomers and analogs, and the like. In one embodiment, this invention encompasses the use of different optical isomers of above described compound. It will be appreciated by those skilled in the art that the compounds useful in the present invention may contain at least one chiral center. Accordingly, the compounds used in the methods of the present invention may exist in, and be isolated in, optically-active or racemic forms. Some compounds may also exhibit polymorphism. It is to be understood that the present invention encompasses the use of any racemic, optically-active, polymorphic, or stereoisomeric form, or mixtures thereof, which possess properties useful in the treatment of Enterococci and Staphylococci—related conditions described and claimed herein. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also he prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes methods utilizing derivatives of the compound. The term "derivatives" includes but is not limited to ether derivatives, acid derivatives, amide derivatives, ester derivatives and the like. In addition, this invention further includes methods utilizing hydrates of the compound.

The term "hydrate" includes but is not limited to hemihydrate, monohydrate, dihydrate, trihydrate and the like.

This invention further includes methods of utilizing metabolites of the compounds. The term "metabolite" means any substance produced from another substance by metabolism or a metabolic process.

As defined herein, "contacting" means that the compound used in the present invention is introduced into a sample containing a sample having a receptor in a test tube, flask, tissue culture, chip, array, plate, microplate, capillary, or the like, and incubated at a temperature and time sufficient to permit binding of the compound to the receptor. Methods for contacting the samples with the compound or other specific binding components are known to those skilled in the art and may be selected depending on the type of assay protocol to be run. Incubation methods are also standard and are known to those skilled in the art.

In another embodiment, the term "contacting" means that the compound used in the present invention is introduced into a patient or a subject for the treatment of Enterococci, Staphylococci and other related diseases and conditions, and the compound is allowed to come in contact with the patient or subject in vivo.

A "patient" or "subject", used equivalently herein, refers to a mammal, preferably a human that has a condition treatable for Enterococci, Staphylococci and other related diseases and conditions by compounds of the present invention.

As used herein, "pharmaceutical composition" means therapeutically effective amounts of the compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active agent sufficient to yield a desired response without undue adverse side effects such as toxicity, irritation, or allergic response. The specific "effective amount" will, obviously, vary with such factors as the particular condition being treated, the physical condition of the patient, the type of animal being treated, the duration of the treatment or diagnosis, the nature of concurrent therapy (if any), and the specific formulations employed and the structure of the compounds or its derivatives. In this case, an amount would be deemed effective if it resulted in treatment of Enterococci, Staphylococci and other related diseases and conditions in a subject. The optimum effective amounts can be readily determined by one of ordinary skill in the art using routine experimentation.

Generally, the present invention teaches various vancomycin analogs that are effective for the treatment of resistant Enterococci or Staphylococci. In a preferred embodiment, the present invention teaches a vancomycin analog having a structure of Formula I,

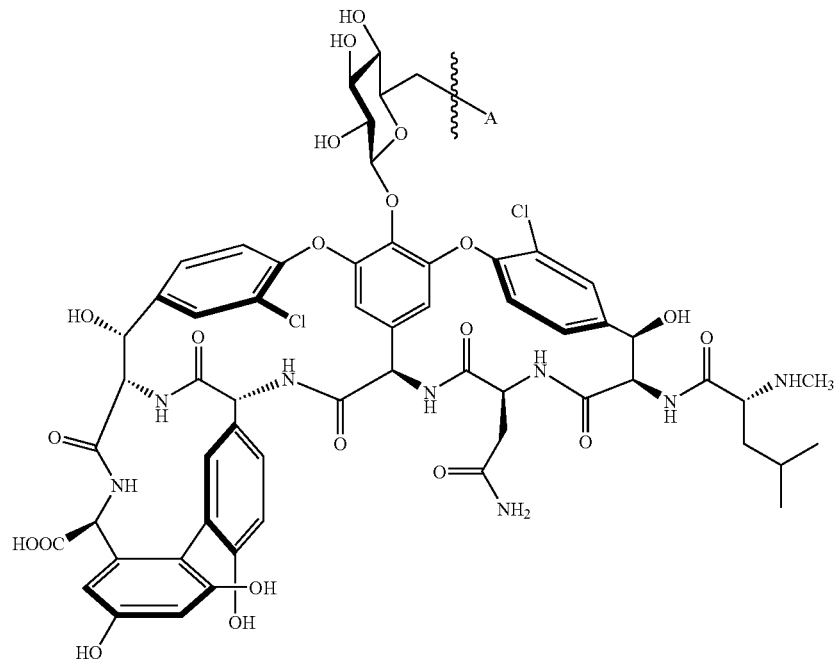

Formula I wherein the structural moiety "A" is selected from the group consisting of:

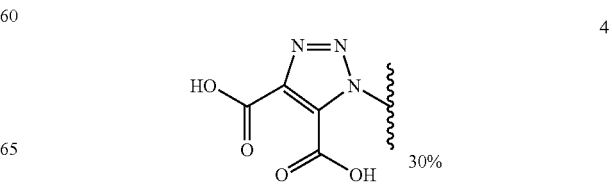

4

30%

-continued
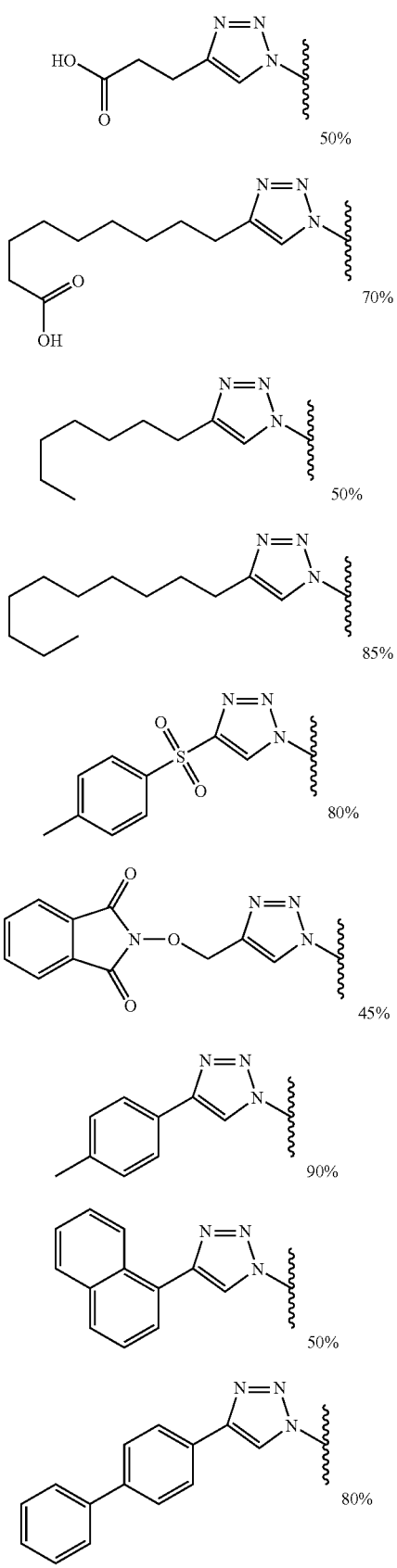
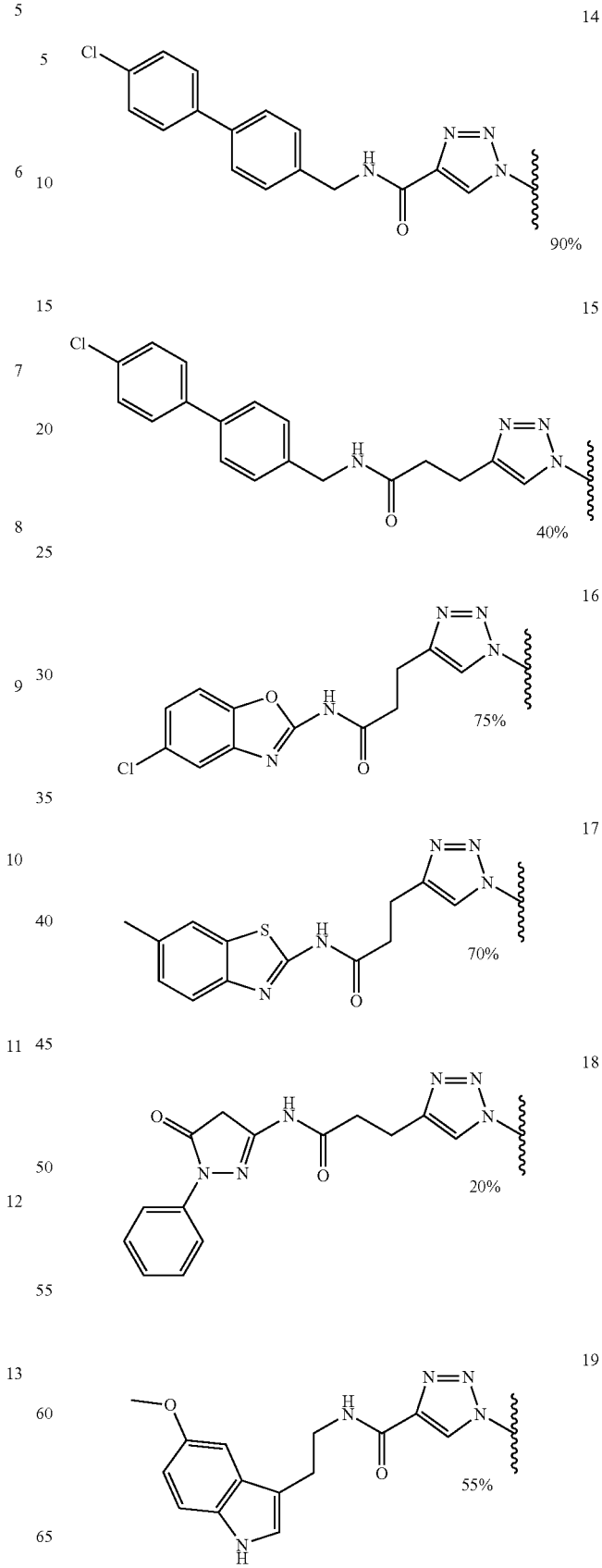

-continued

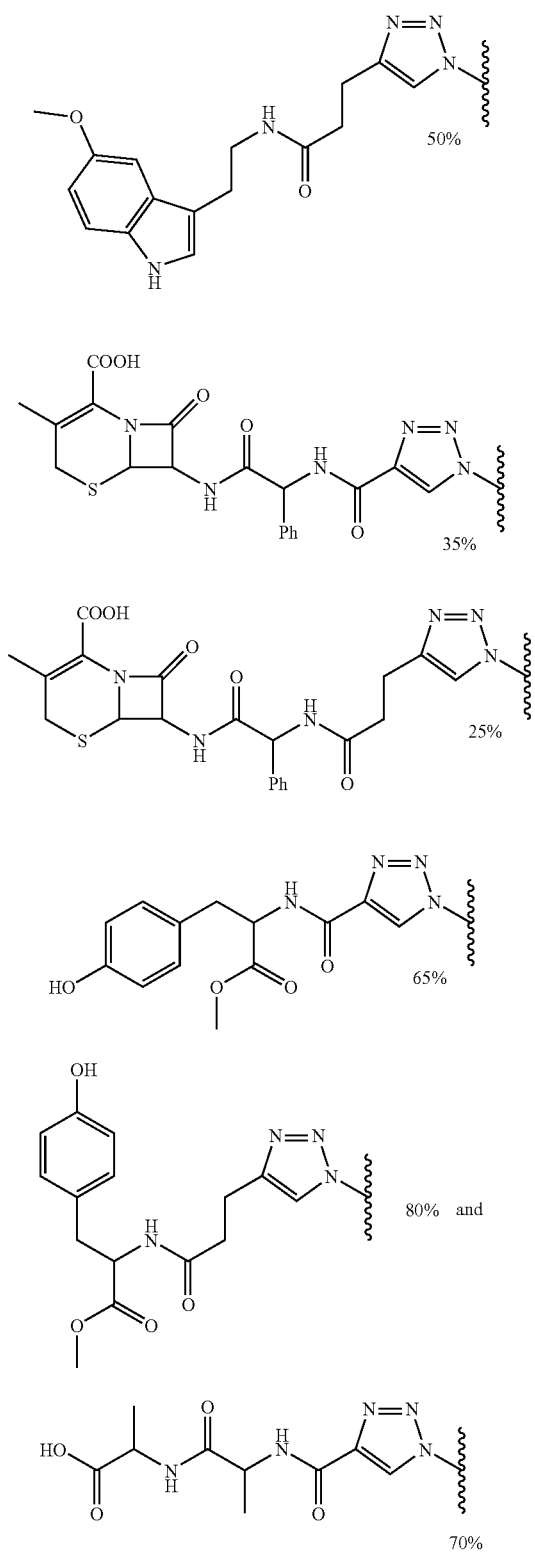

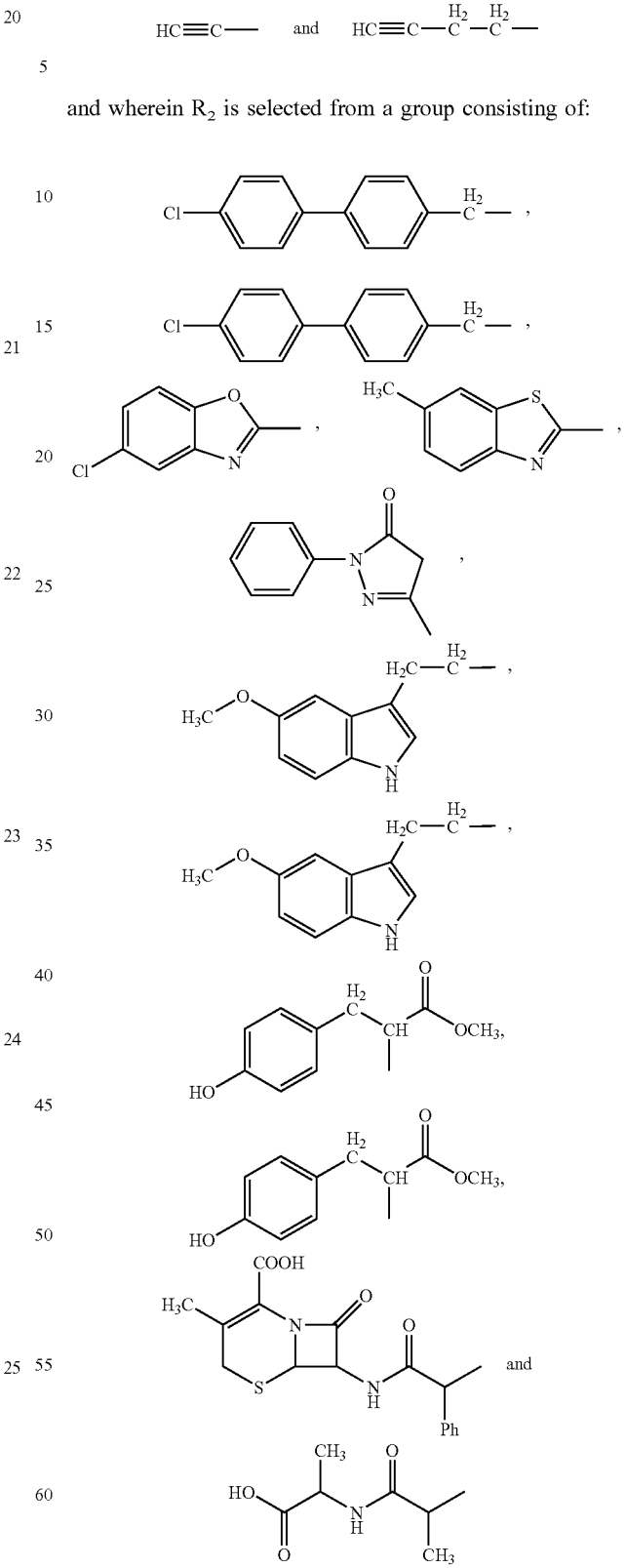

In this embodiment the analog is produced from a dipolar cycloaddition reaction with an alkyne. Preferably, the alkyne is $R_1$—C≡C—$R_2$, wherein $R_1$ is selected from a group consisting of:

and wherein $R_2$ is selected from a group consisting of:

Yet another embodiment of the present invention provides a method for synthesizing a vancomycin analog. The method comprises the steps of:

(a) reacting a vancomycin aglycon with a sugar transferase; and
(b) further reacting the resulting compound from step (a) with an alkyne via a 1,3 dipolar cycloaddition to result in a vancomycin analog, such that the resulting vancomycin analog from step (b) has a structure of Formula I, as shown above and the structural moiety "A" is selected from the group consisting of:
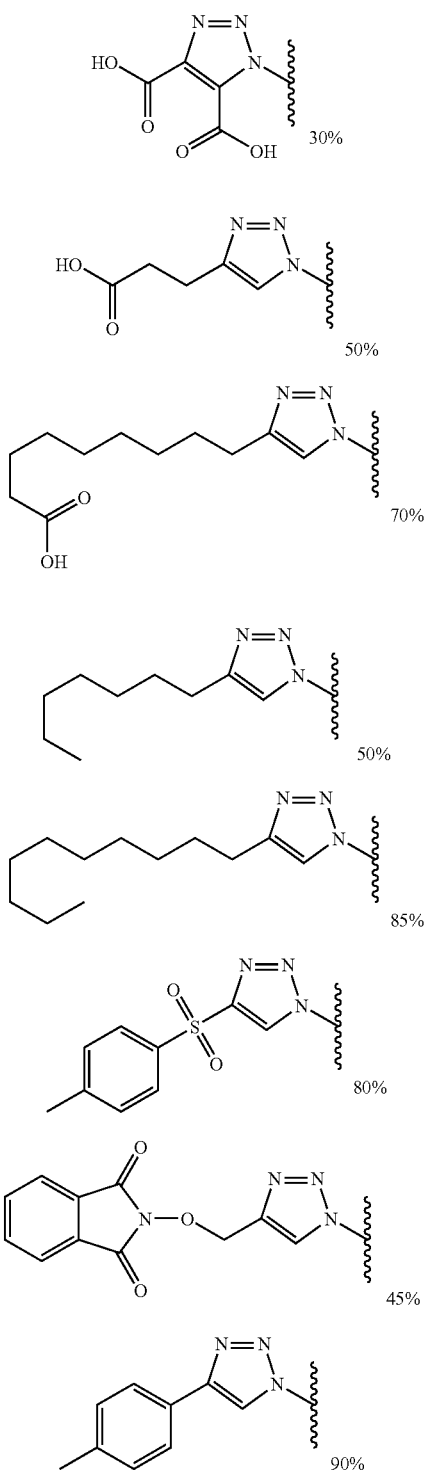
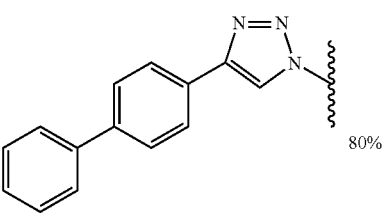
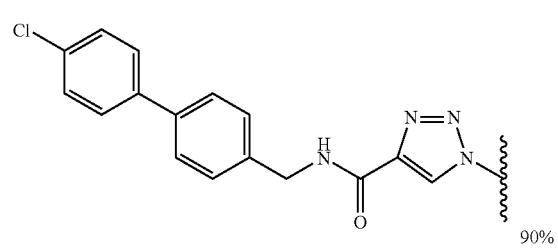
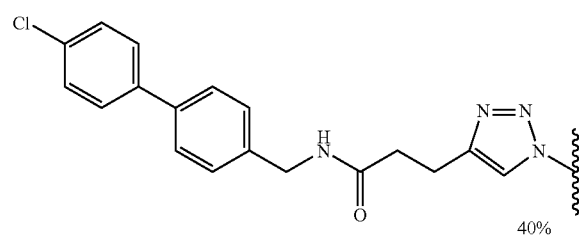
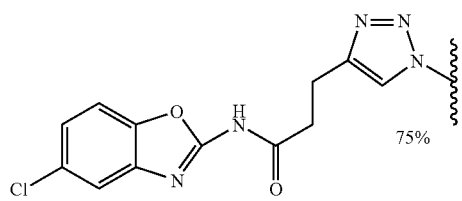
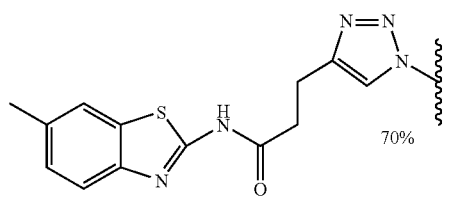
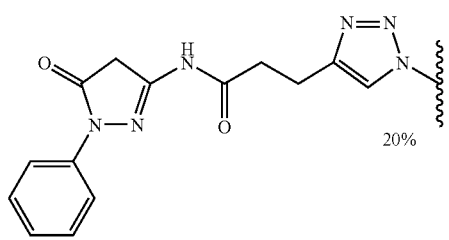

-continued
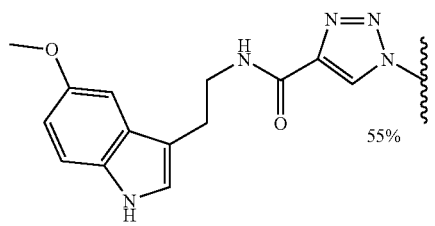
55%
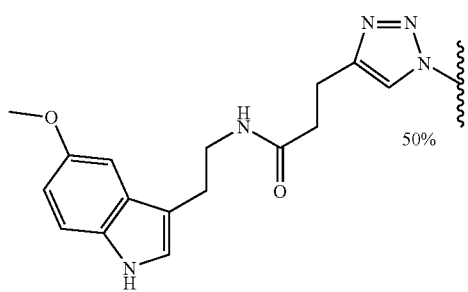
50%
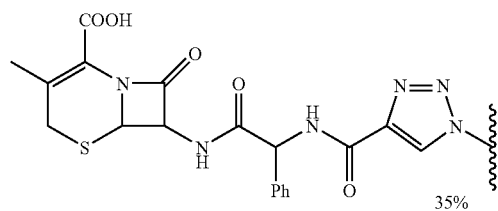
35%
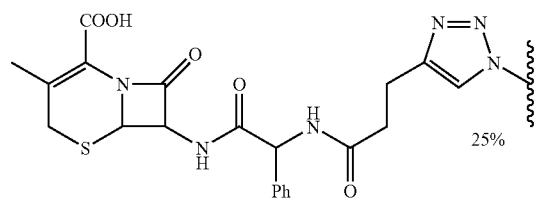
25%
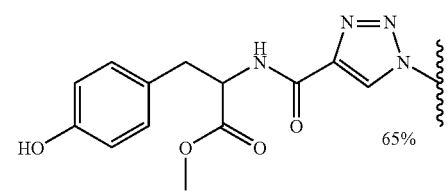
65%
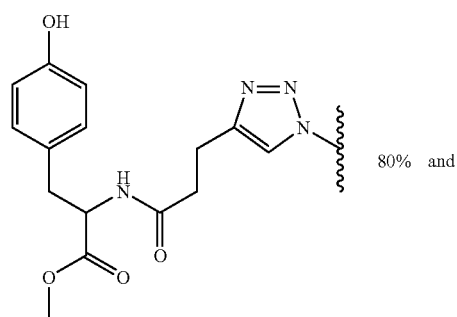
80% and
-continued
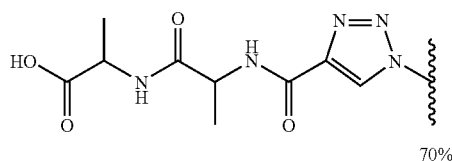
70%
In this embodiment as well, the alkyne is $R_1$—C≡C—$R_2$, wherein $R_1$ is selected from a group consisting of:
and wherein $R_2$ is selected from a group consisting of:
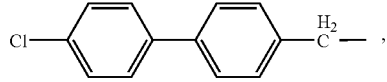
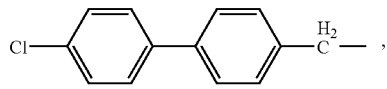
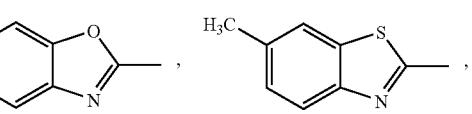
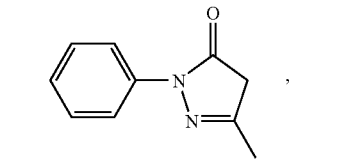
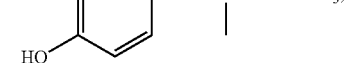
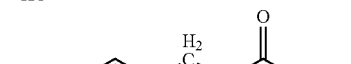

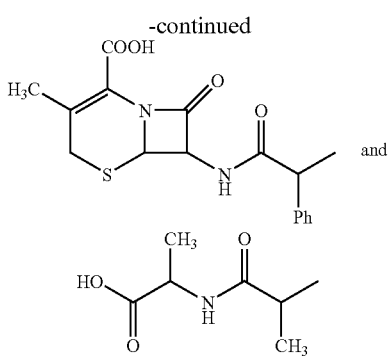

Preferably, in this method, the sugar transferase is GtfE.

Yet another embodiment of the present invention provides the use of the vancomycin analog of claim 1, salt or prodrug thereof for the production of a pharmaceutical composition for the treatment of vancomycin resistant Enterococci or vancomycin resistant Staphylococci.

Another embodiment of the present invention provides a meth od for prevention and/or treatment of vancomycin resistant Enterococci or vancomycin resistant Staphylococci in a subject. This method comprises the step of administering to the subject an effective amount of the vancomycin analog of claim 1, a pharmaceutically acceptable salt, or a prodrug thereof.

The present invention also provides a pharmaceutical composition comprising: (a) the vancomycin analog of claim 1; or (b) a pharmaceutically acceptable salt of said analog; or (c) a pharmaceutically acceptable prodrug of said analog; and (d) a pharmaceutically-acceptable carrier.

Pharmaceutical compositions as described in the present inventions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance.

Controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the skin, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, transmucosally, transdermally, intramuscularly, intravenously, intradermally, subcutaneously, intraperitonealy, intraventricularly and intracranially.

The pharmaceutical preparation can comprise the compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the compound can be administered to a subject by, for example, subcutaneous implantation of a pellet. In a further embodiment, a pellet provides for controlled release of the compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

Further, as used herein "pharmaceutically acceptable carriers" are well known to those skilled in the art and include, but are not limited to, 0.01-0.1 M and preferably 0.05 M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The pharmaceutical preparations administrable by the invention can be prepared by known dissolving, mixing, granulating, or tablet-forming processes. For oral administration, the compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For example, pharmaceutically acceptable salts for topical administration to body surfaces using, creams, gels, drops, and the like, include the compounds or their physiologically tolerated derivatives such as salts, esters, N-oxides, and the like that are prepared and applied as solutions, suspensions, or emulsions in a physiologically acceptable diluent with or without a pharmaceutical carrier.

For use in medicine, the salts of the compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The following Examples are offered by way of illustration and not by way of limiting the scope of the present invention.

EXAMPLES

Glycorandomization is a process utilizing chemical synthesis to provide a repertoire of unique sugar precursors to three promiscuous enzymes which activate (anomeric sugar kinases, GalK; and nucleotidylyltransferases, Ep) and attach (glycosyltransferases, GtfE), these carbohydrate libraries to various complex natural product aglycons, as shown in FIG. 1. The entire process is then followed by downstream chemoselective ligation for further library diversification. This present extension of vancomycin glycorandomization surprisingly reveals a variety of diverse substitutions upon the first sugar attached to vancomycin are tolerated to present analogs that rival the parent natural product.

Figure 2:
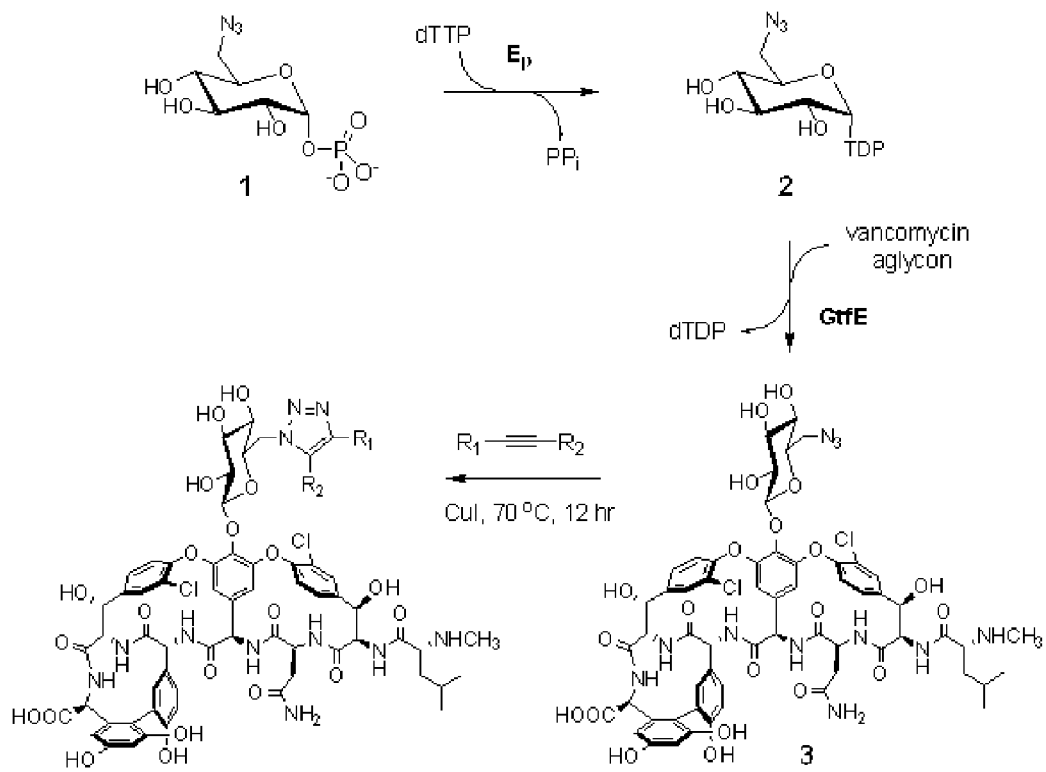
FIG. 2 depicts an outline of the vancomycin glycorandomization process.

An engineered *Salmonella* $E_p$ mutant (L89T) was employed to convert 6-azido glucose-1-phosphate (FIG. 2, 1) to the desired nucleotide sugar 2. Specifically, incubation of 4.2 mM 1, 4.5 mM dTTP, 250 U $E_p$, 40 U inorganic pyrophosphatase in pH 8.0 Tris-HCl buffer (3.8 mL) at 37° C. for 2 hr, led to the production of 2 in >95% yield based upon HPLC analysis. To a portion of this solution (200 µL) was added an equal volume of 2 mM vancomycin aglycon and 20 U purified vancomycin glucosyltransferase GtfE in 150 mM tricine-NaOH buffer, pH 9, and the reaction mixture was incubated for an additional 12 hr at 37° C. to provide the starting material 3 in 58±5% yield for the intended studies. Compound 3 was then further diversified, via 1,3-dipolar cycloaddition, as illustrated in FIG. 2. Regioselectivity of this Huisgen coupling was controlled by the addition of Cu(I) to give the preferred 1,4-disubstituted 1,2,3-triazole in the presence of excess alkyne. Specifically, the dipolar cycloaddition reactions were accomplished at 70° C. in either methanol or $H_2O$-DMSO (4:1 or 2:1) with 150:5:1 alkyne-CuI-azide (3.75 mM) molar ratio. After 12 hr, reaction progress was assessed via LC-MS and HRMS was subsequently utilized to confirm product formation.

Figure 3:
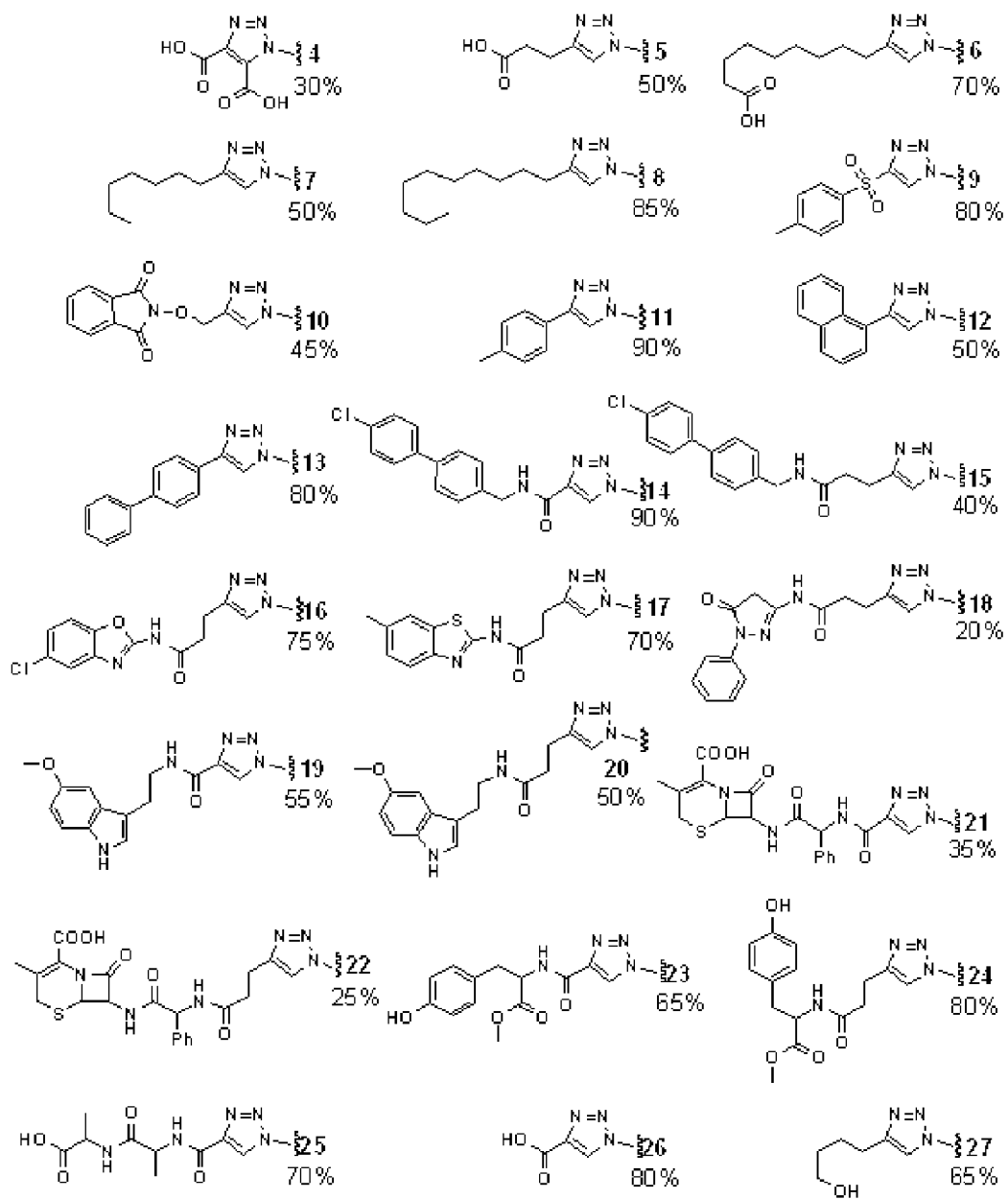
FIG. 3 depicts products of azido-3 Huisgen 1,3-dipolar cycloaddition reactions.

For the present study, 24 different alkynes were utilized and their structures with representative cycloaddition yields are presented in FIG. 3. Of these 24, 2 (26 and 27) were previously reported and have been included for comparison to the earlier study. A number of factors were considered in selecting representative alkynes for the current study. For example, aliphatic and/or 'lipid-like' alkynes (FIG. 3, 6-8, 26, 27) were selected to mimic and enhance the membrane anchor component of various bioactive glycopeptide antibiotics. Two of these (FIG. 3, 26 and 27) were previously shown to have either enhanced antibiotic activity or very distinct species preference. A variety of aromatic analogs were targeted (FIG. 3, 9-20, 23, 24), some of which were based upon the known ability of chloro-biphenyl substitution to alter glycopeptide mechanism of action (FIG. 3, 12-15). The remainder within this set were loosely based upon the reported enhancement of glycopeptide antibiotic dimerization via substitution with certain hydrogen-bonding pharmacophores (FIG. 3, 16-25) and/or the ease of incorporating potential antiviral pharmacophores (FIG. 3, 17). In addition, the simplicity of this chemistry also allows one to probe the potential advantage of covalently attaching two antibiotics with distinct mechanisms of cell wall biosynthesis inhibition (for example, a glycopeptide and β-lactam, FIG. 3, 21 and 22) or the potential of enhancing interactions with alternative targets (for example, by appending with D-ala-D-ala, FIG. 3, 25 ). In most cases, the reactions proceeded as expected and even a few representative alkynes lacking adjacent electron-withdrawing substituents led to products (8 and 24, for example) in high yield.

The entire set of analogs were tested for their antibacterial activity and those analogs showing favorable activities against methicillin-resistant *S. aureus*, vancomycin-sensitive *E. faecalis* and/or *E. faecium* are highlighted in FIG. 4. In comparison to the parent natural product or 3, three analogs (6, 7, and 26) show slightly better activity against all three pathogens. While the carboxylate of 26 was previously shown to be essential for its enhanced anti-MRSA activity, a comparison of 4-8, 26 and 27 may implicate side chain length as favoring desired activities. Interestingly, triazole substitution via long alkyl chains (e.g. 7 and 8 ) favors *S. aureus* activity while a carboxylate extension (6) to this unit slightly favors activity toward *Enterococcus*. Covalent fusion of two cell wall directed agents—a glycopeptide and β-lactam—presented chimeric natural product analogs (21 and 22), one of which with slightly enhanced activity. However, these chimera appear to be quite sensitive to linker length as the synergistic effects can be abolished via the simple addition of an ethyl bridge. Also notable, the chlorobiphenyl and fused aromatic variants 11-15 surprisingly lacked beneficial contributions.

Overall, the rapid diversification of glycopeptides via glycorandomization reveals significantly diverse substitutions are tolerated and can lead to analogs that rival the parent natural product. The present invention also illustrates there may be a synergistic effect of mechanistically-related natural product core scaffold chimera and highlights the benefits of glycorandomization in generating such complex natural product analogs.

Material and Methods

The 6-Azido glucose-1-phosphate was prepared chemically, Ep and GtfE were overexpressed, purified and used as biocatalysts as described before. Vancomycin aglycon was prepared by hydrolysis of vancomycin in trifluoroacetic acid at room temperature for 5 hr. Other enzyme or reagents were purchased from Sigma or Aldrich. Alkynes 4-13, 26 and 27 for the present studies were purchased from Aldrich.

Figure 5:
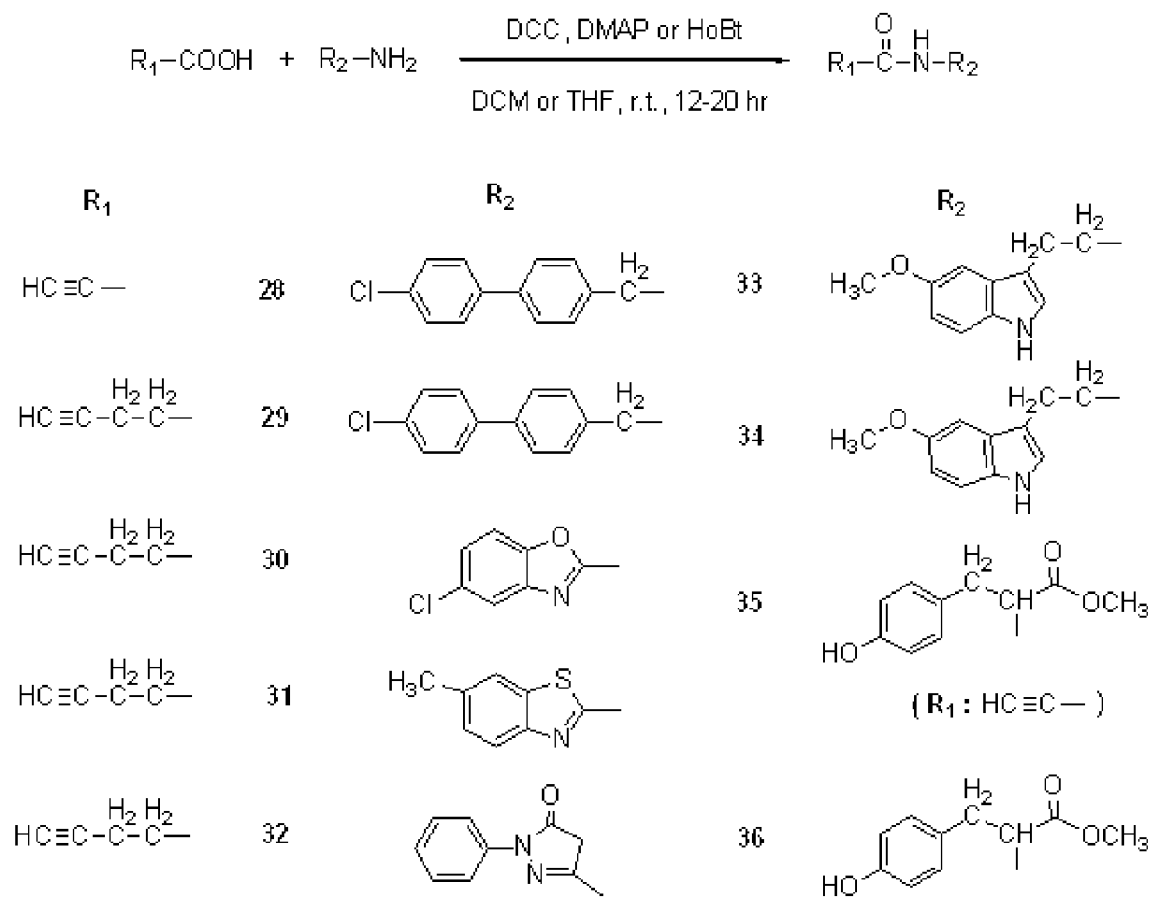
FIG. 5 depicts general synthesis outline of alkynes via standard amine-acid condensation.
Figure 6:
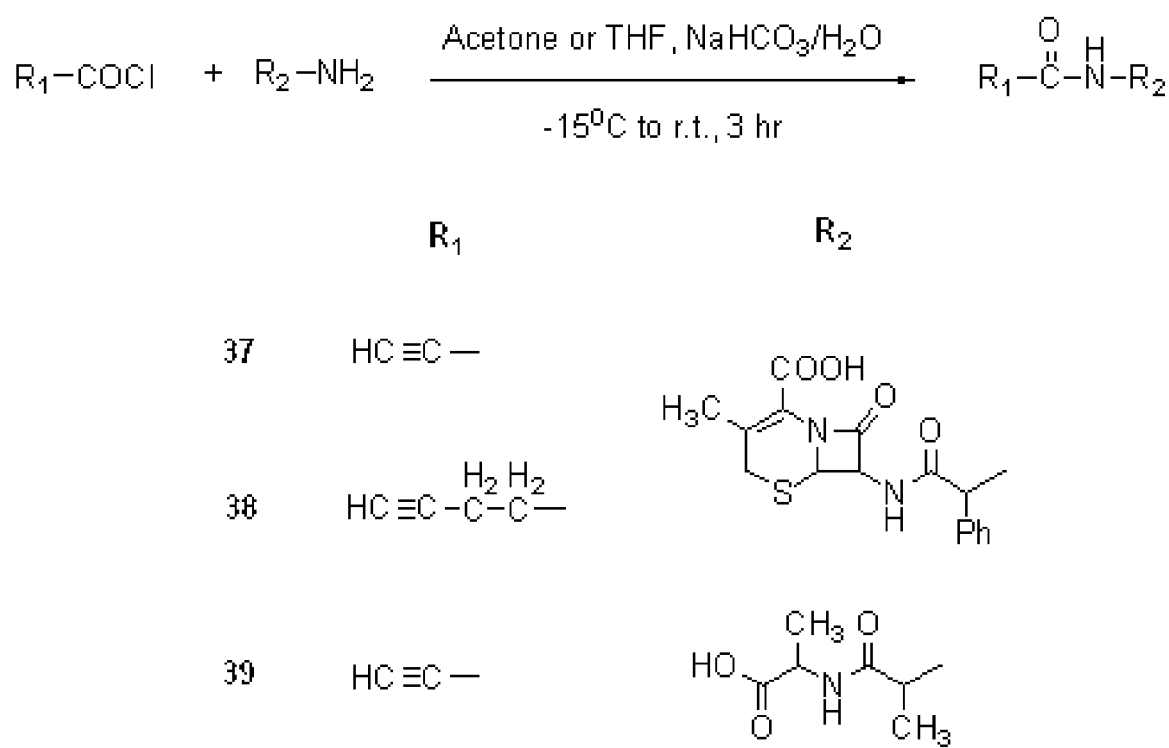
FIG. 6 depicts general synthesis of alkynes via standard amine-acyl chloride condensation.

Synthesis of alkynes via standard amine-acid condensation. (Outline of the synthesis is provided in FIG. 5). To a mixture of amine hydrochloride (1.0 mmol), dicyclohexyl carbodiimide (DCC, 248 mg, 1.2 mmol), dimethylamino pyridine (DMAP, 12 mg, 0.1 mmol) in 6.0 mL anhydrous $CH_2Cl_2$ was added the organic acid (1.1 mmol), and the reaction was stirred at room temperature for 20 hr. Hexane (4.0 mL) was added and the mixture was centrifuged (2770 g, 5 min), the products from the supernatant resolved via flash chromatography (hexane-EtOAc, gradient of 1:1 to 1:2) to give the desired amide (average yield=73% yield). HOBt can also be used instead of DMAP for condensation reaction.

Amide 28 (for the preparation of 14). $^1$H-NMR [$(CD_3)_2$CO]: δ2.82 (s, 1H), 6.46 (br, NH), 4.50 (d, 2H), 7.37 (m, 4H), 7.48 (m, 4H); $^{13}$C-NMR [$(CD_3)_2$CO]: δ133.737, 129.148 (2C), 127.513 (2C), 139.717, 136.579, 128.621 (2C), 128.445 (2C), 139.129, 43.672, 152.326, 80.346, 73.999. MS: calculated for $C_{16}H_{12}NOCl$ 269.1, found m/z [M+H]$^+$ 270.1.

Amide 29 (for the preparation of 15). Rf (hexane/EtOAc=1/2): 0.6; $^1$H—NMR [$(CD_3)_2$CO]: δ 2.00 (t, 1H), 2.57 (m, 2H), 2.46 (t, J=7.2 Hz, 2H), 6.17 (br, NH), 4.49 (d, 2H), 7.35 (d, 2H), 7.44 (dd, 4H), 7.50 (d, 2H); $^{13}$C-NMR [$(CD_3)_2$CO]: δ 133.661, 129.132 (2C), 127.406 (2C), 139.420, 137.762, 128.453 (2C), 128.498 (2C), 139.282, 43.497, 171.152, 35.546, 15.132, 83.156, 69.662. MS: calculated for $C_{18}H_{16}NOCl$ 297.1, found m/z[M+H]$^+$ 298.1.

Amide 30 (for the preparation of 16). $^1$H-NMR [$(CD_3)_2$CO]: δ 2.05 (1H), 2.67 (2H), 3.02 (2H), 7.26 (1H), 7.39 (1H), 7.59 (1H); $^{13}$C-NMR [$(CD_3)_2$CO]: δ 163.377, 146.560, 144.307, 128.093, 119.517, 115.232, 108.619, 173.211, 34.088, 14.792, 69.232, 80.376. MS: calculated for $C_{12}H_9N_2O_2Cl$ 248.0, found m/z[M+H]$^+$ 249.0; [M–H]$^-$ 247.1.

Amide 31 (for the preparation of 17). $^1$H-NMR [$(CD_3)_2$CO]: δ 2.00 (1H), 2.40 (3H), 2.56 (2H), 2.64 (2H), 7.10 (1H), 7.37 (2H); $^{13}$C-NMR [$(CD_3)_2$CO]: δ 21.469, 149.232, 132.407, 131.300, 127.481, 121.241, 118.561, 166.423, 172.150, 34.132, 14.657, 69.064, 78.105. MS: calculated for $C_{13}H_{12}N_2OS$ 244.1, found m/z[M+H]$^+$ 245.0; [M–H]$^-$ 243.0.

Amide 32 (for the preparation of 18). $^1$H-NMR [$(CD_3)_2$CO]: δ 1.98 (1H), 2.48 (2H), 2.59 (2H), 3.50 (2H), 7.30 (1H), 7.38 (2H), 7.76 (2H); $^{13}$C-NMR [$(CD_3)_2$CO]: δ 127.809 (2C) 125.396 (2C), 139.120, 116.094, 166.562, 155.488, 39.354, 172.810, 33.467, 14.405, 69.362, 82.658. MS: calculated for $C_{14}H_{13}N_3O_2$ 255.1, found m/z[M+H]$^+$ 256.0; [M–H]$^-$ 254.0.

Amide 33 (for the preparation of 19). $^1$H-NMR [$(CD_3)_2$CO]: δ 2.00 (1H), 2.88 (2H), 3.54 (2H), 6.78 (1H), 6.93 (d, 1H), 7.00 (d, 1H), 7.19 (d, 1H), 3.78 (s, 3H); $^{13}$C-NMR [$(CD_3)_2$CO]: δ 56.127, 154.013, 131.956, 127.848 123.563, 112.512, 112.306, 111.962, 100.598, 162.971, 40.570, 25.143, 73.960, 77.748. MS: calculated for $C_{14}H_{14}N_2O_2$ 242.1, found m/z[M+H]$^+$ 243.1.

Amide 34 (for the preparation of 20). $^1$H-NMR [$(CD_3)_2$CO]: δ 1.93 (1H), 2.46 (2H), 2.88 (2H), 2.30 (2H), 3.55 (2H), 6.82 (1H), 6.93 (1H), 7.00 (1H), 7.20 (1H), 3.80 (s, 3H); $^{13}$C-NMR [$(CD_3)_2$CO]: δ 56.257, 127.924, 123.487, 112.474 112.382, 112.352, 100.820, 154.089, 131.979, 40.119, 25.486, 171.654, 35.491, 15.153, 69.797, 83.254. MS: calculated for $C_{16}H_{18}N_2O_2$ 270.1, found m/z[M+H]$^+$ 271.1.

Amide 35 (for the preparation of 23). $^1$H-NMR [$(CD_3)_2$CO]: δ 1.86 (1H), 2.92 (m, 2H), 4.69 (m, 1H), 3.59 (s, 3H), 6.71 (d, 2H), 6.84 (d, 2H); $^{13}$C-NMR [$(CD_3)_2$CO]: δ 156.449, 130.360 (2C), 115.926 (2C), 126.343, 31.757, 52.667, 171.517, 54.149, 163.177, 74.975, 77.020. MS: calculated for $C_{13}H_{13}NO_4$ 247.1, found m/z[M+H]$^+$ 248.1.

Amide 36 (for the preparation of 24). $^1$H-NMR [$(CD_3)_2$CO]: δ 1.98 (1H), 2.45 (m, 4H), 4.81 (m, 1H), 2.96 (m, 2H), 3.69 (s, 3H), 6.79 (d, 2H), 6.94 (d, 2H); $^{13}$C-NMR [$(CD_3)_2$CO]: δ 156.304, 130.437 (2C), 115.865 (2C), 126.733, 31.894, 52.533, 172.349, 53.828, 171.654, 35.140, 14.901, 82.865, 69.797. MS: calculated for $C_{15}H_{17}NO_4$ 275.1, found m/z[M+H]$^+$ 276.1.

Synthesis of alkynes via standard amine-acyl chloride condensation. (See FIG. 6) Acyl chloride (5.6 mmol) in dry acetone (2 mL) was added dropwise at −15° C. to a solution of amine (5.5 mmol) and sodium bicarbonate (1.38 g, 16.4 mmol) in 50:50 $H_2O$:acetone (48 mL). After stirring for another 1 hr at 0° C. and room temperature for 1 hr, the solution was extracted with ether (40×2 mL). The aqueous layer was overlayed with 20 mL ethyl acetate and adjusted with 10% HCl to pH 2, and the resulted oily mixture was extracted with ethyl acetate (40×3 mL). The organics were washed by brine (10×2 mL), dried (anhydrous sodium sulphate), filtered and evaporated to dryness to give pure material (50% average yield). For this work, propiolyl and 4-pentynoic chloride were prepared from the corresponding propiolic and 4-pentynoic acid with phosphorus pentachloride and thionyl chloride, respectively.

Amide 37 (for the preparation of 21). $^1$H-NMR [(CD$_3$)$_2$CO]: δ 2.07 (s, 1H), 3.49, 3.23 (d, J=18 Hz, 2H), 5.00, 5.75 (d, J=4.6 Hz, 2H), 5.78 (s, 1H), 2.31 (t, 1H), 7.35 (m, 3H), 7.54 (dd, 2H); $^{13}$C-NMR [(CD$_3$)$_2$CO]: δ 170.734, 123.528, 19.584, 131.983, 30.225, 58.116, 59.858, 164.754, 163.776, 57.505, 152.007, 78.210, 75.529, 139.398, 128.561(2C), 129.470(2C), 129.104. MS: calculated for C$_{19}$H$_{17}$N$_3$O$_5$S 399.1, found m/z[M+H]$^+$ 400.2.

Amide 38 (for the preparation of 22). $^1$H-NMR [(CD$_3$)$_2$CO]: δ 2.32 (t, 1H), 2.46 (m, 2H), 2.55 (m, 2H), 2.09 (s, 3H), 3.55, 3.28 (d, J=18 Hz, 1H), 5.02 (d, J=4.8Hz, 1H), 5.76 (dd, J=4.8, 8.4 Hz, 1H), 7.78 (d, J=8.4 Hz, NH), 5.75 (d, J=8.4 Hz, 1H), 8.25 (d, J=8.4 Hz, NH), 7.32 (m, 3H), 7.51 (dd, 2H); $^{13}$C-NMR [(CD$_3$)$_2$CO]: δ 170.955, 123.635, 19.854, 131.853, 28.035, 58.216, 59.926, 165.075, 163.769, 57.589, 171.589, 35.426, 15.150, 84.197, 70.282, 139.398, 128.752, 128.401 (2C), 129.348 (2C). MS: calculated for C$_{21}$H$_{21}$N$_3$O$_5$S 427.1, found m/z[M+H]$^+$ 428.1, [2M+H]$^+$ 855.2.

Amide 39 (for the preparation of 25). $^1$H-NMR [(CD$_3$)$_2$CO]: δ 1.92 (s, 1H), 4.16 (m, 2H), 1.38 (m, 3H), 1.40 (m, 3H); $^{13}$C-NMR [(CD$_3$)$_2$CO]: δ 180.061, 51.469, 17.277, 170.170, 49.344, 16.678, 164.250, 73.622, 78.495. MS: calculated for C$_9$H$_{12}$N$_2$O$_4$ 212.1, found m/z[M+Na]$^+$ 235.0, [M−H]$^−$ 210.9.

Overall FIG. 7 provides product characterization of certain analogs.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A vancomycin analog having a structure of formula I,

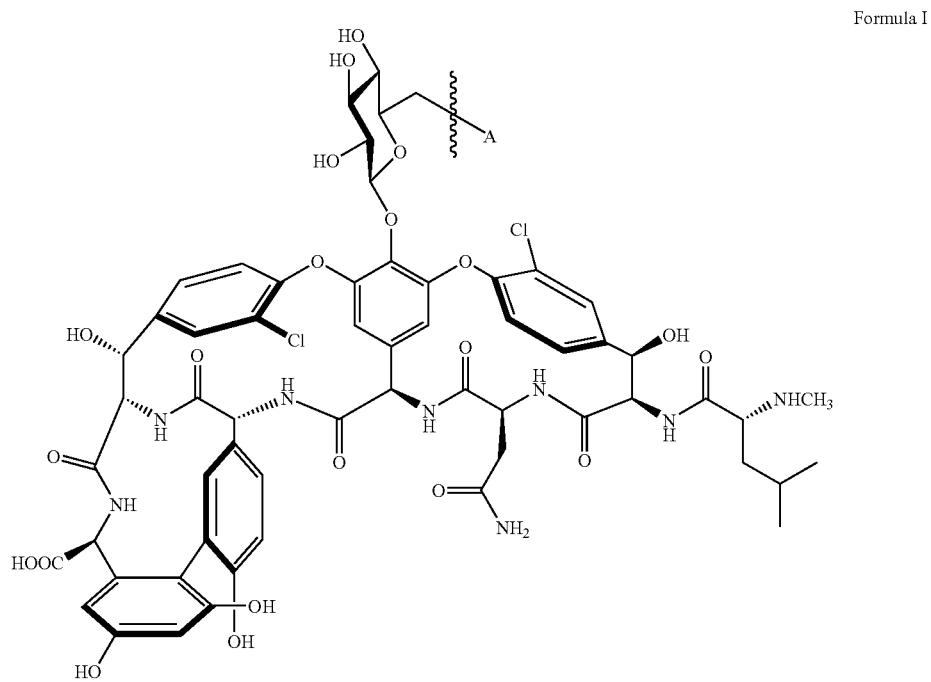

Formula I wherein the structural moiety "A" is selected from the group consisting of:

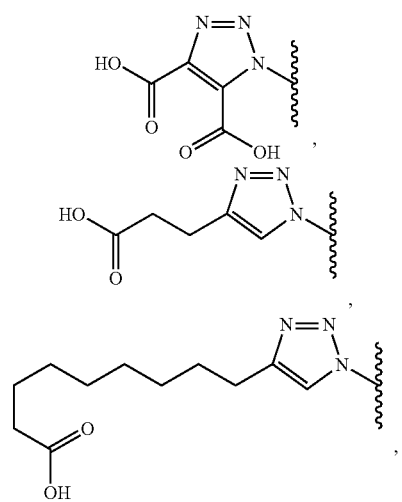

-continued
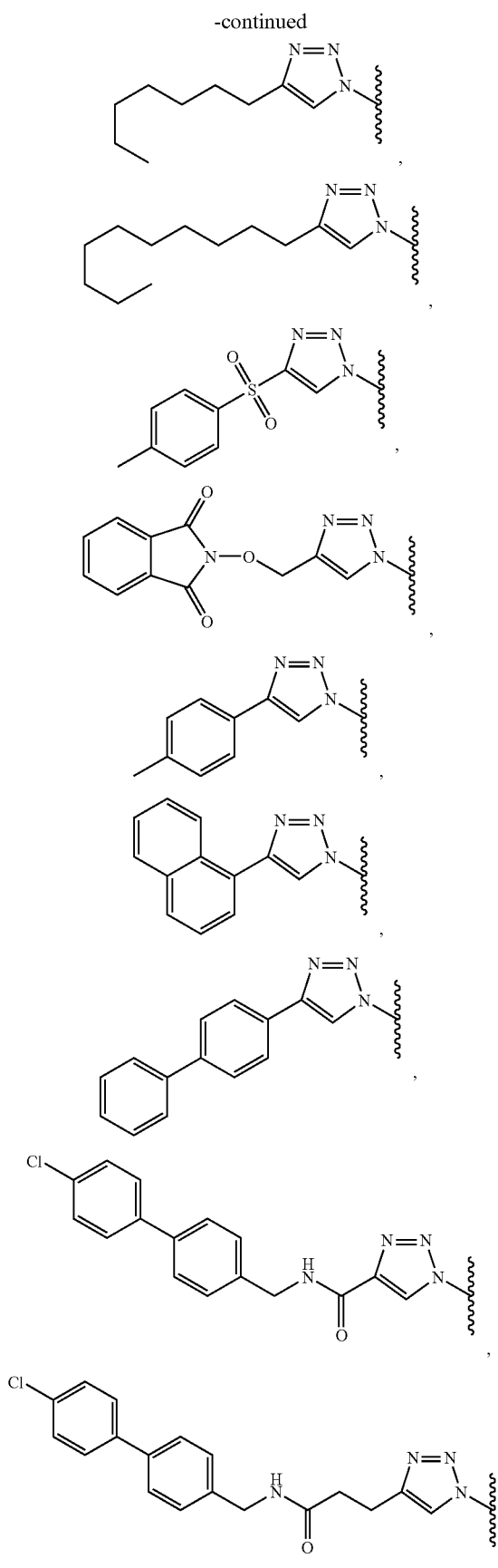
-continued
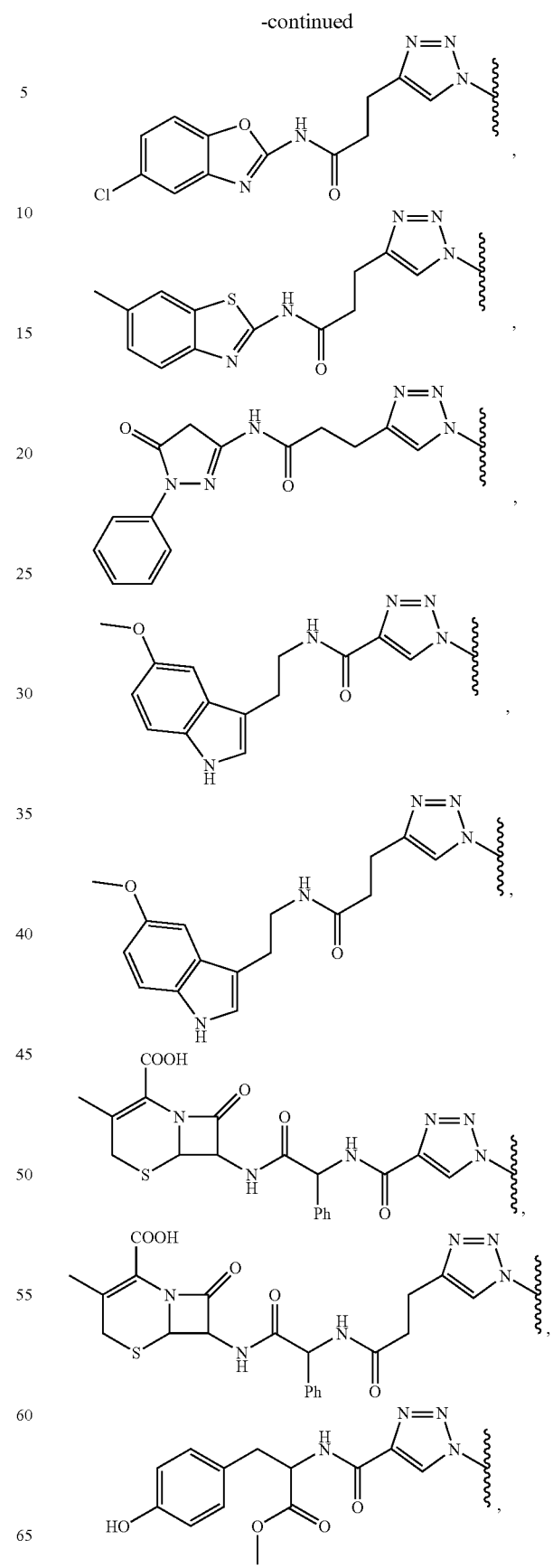

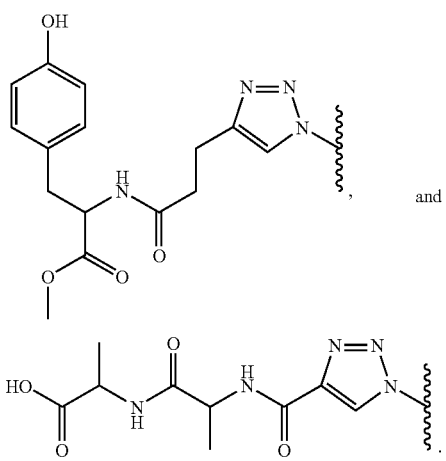

2. The vancomycin analog of claim 1, wherein the analog is produced from a dipolar cycloaddition reaction with an alkyne, wherein the alkyne is $R_1\text{—}C\equiv C\text{—}R_2$, wherein $R_1$ is selected from the group consisting of:

and wherein $R_2$ is selected from the group consisting of:

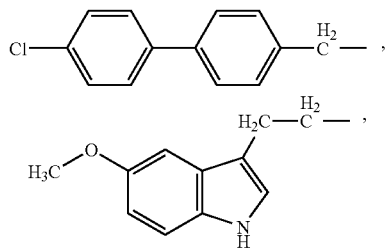

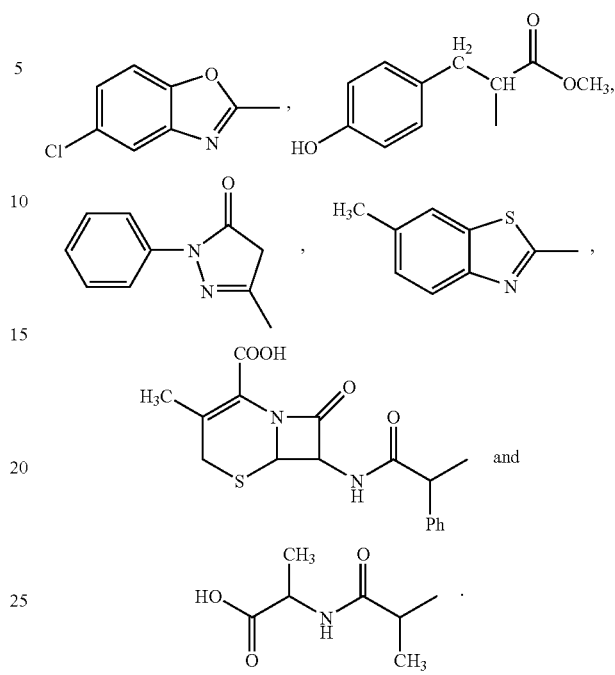

3. A method for the treatment of vancomycin resistant Enterococci or vancomycin resistant Staphylococci in a subject, comprising the step of administering to said subject an effective amount of the vancomycin analog of claim 1, a pharmaceutically acceptable salt, or a prodrug thereof.

4. A pharmaceutical composition comprising:
 (a) the vancomycin analog of claim 1; or
 (b) a pharmaceutically acceptable salt of said analog; or
 (c) a pharmaceutically acceptable prodrug of said analog; and
 (d) a pharmaceutically-acceptable carrier.

* * * * *

UNITED STATES PATENT AND TRADEMARK OFFICE
CERTIFICATE OF CORRECTION

PATENT NO. : 7,259,141 B2
APPLICATION NO. : 10/908624
DATED : August 21, 2007
INVENTOR(S) : Jon S. Thorson Page 1 of 1

It is certified that error appears in the above-identified patent and that said Letters Patent is hereby corrected as shown below:

In the Specification

Column 1, Lines 17-19:
Delete the phrase:
"This work was supported in part by the National Institutes of Health (GM58196, CA84374, and AI52218). The Federal Government may have certain rights in this invention."
And replace with:
--This invention was made with government support under AI052218 awarded by the National Institutes of Health. The government has certain rights in the invention.--.

Signed and Sealed this
Eighth Day of December, 2020

Andrei Iancu
*Director of the United States Patent and Trademark Office*